(12) United States Patent
Lomax

(10) Patent No.: US 11,255,102 B2
(45) Date of Patent: Feb. 22, 2022

(54) SUPPORT-WEIGHT, STRENGTHENING POST, RELATED METHODS OF USE AND INSTALLATIONS

(71) Applicant: Lomax Group Pty Ltd., Hunters Hili (AU)

(72) Inventor: Mark Lomax, Hunters Hill (AU)

(73) Assignee: Lomax Group Pty Ltd., Hunters Hill (AU)

( * ) Notice: Subject to any disclaimer, the term of this patent is extended or adjusted under 35 U.S.C. 154(b) by 0 days.

(21) Appl. No.: 16/923,248

(22) Filed: Jul. 8, 2020

(65) Prior Publication Data

US 2020/0392753 A1    Dec. 17, 2020

Related U.S. Application Data

(63) Continuation of application No. 15/987,071, filed on May 23, 2018, now Pat. No. 10,731,373, which is a continuation-in-part of application No. PCT/AU2017/050797, filed on Aug. 1, 2017, and a continuation-in-part of application No. PCT/AU2016/051204, filed on Dec. 8, 2016.

(30) Foreign Application Priority Data

Nov. 22, 2016    (AU) ................................ 2016904762

(51) Int. Cl.
  *E04H 12/22* (2006.01)
  *E04H 17/20* (2006.01)
  *E04H 17/22* (2006.01)

(52) U.S. Cl.
  CPC ..... *E04H 12/2238* (2013.01); *E04H 12/2246* (2013.01); *E04H 12/2269* (2013.01); *E04H 17/20* (2013.01); *E04H 17/22* (2013.01)

(58) Field of Classification Search
  CPC . E04H 12/2238; E04H 12/2246; E04H 17/20; E04H 17/22; E04H 12/2269
  USPC ................ 248/188.1, 526, 406.2, 217.1, 910
  See application file for complete search history.

(56) References Cited

U.S. PATENT DOCUMENTS

| | | | |
|---|---|---|---|
| 4,573,301 | A | 3/1986 | Wilkinson |
| 4,651,485 | A | 3/1987 | Osborne |
| 4,681,302 | A | 7/1987 | Thompson |
| 5,960,604 | A | 10/1999 | Blanton |
| 7,338,033 | B2 | 3/2008 | Anson et al. |
| 8,863,464 | B2 | 10/2014 | Balducci, Jr. |

(Continued)

FOREIGN PATENT DOCUMENTS

| | | |
|---|---|---|
| AU | 2009202587 A1 | 1/2010 |
| AU | 2012203098 A1 | 12/2012 |

(Continued)

*Primary Examiner* — Muhammad Ijaz
(74) *Attorney, Agent, or Firm* — Carlson, Gaskey & Olds, P.C.

(57) ABSTRACT

There is provided a structure support arrangement for supporting a structure, the structure support arrangement comprising: a body member; a nesting formation defined on the body member and configured to prevent lateral movement of the structure support arrangement in at least one transverse direction when the structure support arrangement is nested with a further structure support arrangement; and a post receiving formation defined on the body member and configured for receiving a support post to support the structure.

18 Claims, 16 Drawing Sheets

(56) References Cited

U.S. PATENT DOCUMENTS

| | | | |
|---|---|---|---|
| 2002/0119870 A1* | 8/2002 | Chen | A63B 21/063 482/93 |
| 2007/0170411 A1* | 7/2007 | Ribak | E01F 13/022 256/32 |
| 2008/0224016 A1* | 9/2008 | Defu | E04H 12/2246 248/523 |
| 2011/0146186 A1 | 6/2011 | Summers | |
| 2014/0054529 A1 | 2/2014 | Whiteley | |
| 2014/0182109 A1 | 7/2014 | Williams | |
| 2017/0259103 A1* | 9/2017 | Simonetti | A63B 21/063 |

FOREIGN PATENT DOCUMENTS

| | | | | |
|---|---|---|---|---|
| AU | 2012203098 B2 | | 12/2012 | |
| AU | 2013100057 B4 | | 2/2013 | |
| AU | 2015100090 A4 | | 2/2015 | |
| AU | 2015100091 A4 | | 2/2015 | |
| AU | 2015101131 B4 | | 10/2015 | |
| AU | 2015101162 A4 | | 10/2015 | |
| AU | 2015101162 B4 | | 10/2015 | |
| AU | 2016200473 A1 | | 8/2016 | |
| AU | 2012203098 B2 | * | 11/2016 | E04H 17/22 |
| AU | 2015101131 B4 | * | 5/2017 | |
| AU | 2017208718 A1 | | 7/2017 | |
| DE | 19511906 A1 | | 10/1996 | |
| DE | 202004016430 U1 | | 1/2005 | |
| DE | 202004016430 U1 | * | 1/2005 | E04H 12/2238 |
| EP | 1447497 A1 | | 8/2004 | |
| FR | 2805554 A1 | | 8/2001 | |
| FR | 2918400 B1 | | 1/2009 | |
| GB | 2360531 A | | 9/2001 | |
| GB | 2391560 B | | 3/2005 | |
| GB | 2437285 B | | 10/2007 | |
| GB | 2458312 A | | 9/2009 | |
| GB | 2466876 A | | 7/2010 | |
| GB | 2518294 A | | 3/2015 | |
| NL | 1008592 C2 | | 9/1999 | |
| WO | 2007114756 A1 | | 10/2007 | |
| WO | 2016015087 A1 | | 2/2016 | |

* cited by examiner

SUPPORT-WEIGHT, STRENGTHENING POST, RELATED METHODS OF USE AND INSTALLATIONS

CROSS REFERENCE TO RELATED APPLICATION

This application is a continuation of U.S. patent application Ser. No. 15/987,071 filed May 23, 2018 that is a Continuation-in-part Application of prior patent application PCT/AU2016/051204 filed Dec. 8, 2016, which designates the United States of America, and claims priority from AU Patent Application No. 2016904762 filed Nov. 22, 2016; and a Continuation-in-part Application of prior Patent Application PCT/AU2017/050797 filed Aug. 1, 2017, which designates the United States of America, and claims priority therefrom, all of which applications are incorporated herein by reference for all purposes as if fully set forth herein.

BACKGROUND

The present invention relates to a support arrangement for supporting structures.

In particular, although not exclusive, this invention relates to a support arrangement for supporting structures such as hoardings and panels.

The present invention also relates to a support-weight, a strengthening post, related methods of use of the support-weight and/or strengthening post and hoarding and/or fencing installations including a support-weight and/or a strengthening post.

Structures such as hoardings, panels often time need to be erected to form a "wall" or "fence" at a construction site or renovation site to fence off areas in which construction or renovation is being carried out. The structure is typically made of wood, wooden composites, or plastics and is typically screwed to a support post. However, such an arrangement is not always able to provide sufficient stability to the structure especially during windy conditions or when the structure is pushed by people accidentally. Moreover, if the structures are temporary installations, it is generally not possible to fix the support posts without making any indentations on the ground.

It should be noted that although this present invention is described with reference to supporting hoardings or panels used at a construction or renovation site, the present invention can also be used to support structures such as billboards, advertisement boards, or screens, etc., without departing from the scope of the present invention.

It is to be understood that, if any prior art information is referred to herein, such reference does not constitute an admission that the information forms part of the common general knowledge in the art, in Australia or any other countries.

SUMMARY

These and other features of the present invention can be best understood from the following specification and drawings, the following of which is a brief description.

According to a first aspect of the present invention, there is provided a structure support arrangement for supporting a structure, the structure support arrangement comprising a body member, a nesting formation defined on the body member and configured to prevent lateral movement of the structure support arrangement in at least one transverse direction when the structure support arrangement is nested with a further structure support arrangement and a post receiving formation defined on the body member and configured for receiving a support post to support the structure. The nesting formation makes the structure support arrangement and the further structure support arrangement stackable and prevents displacement between the structure support arrangement and the further structure support arrangement in transverse directions.

Preferably, the post receiving formation is any one or more selected from an aperture and a recess.

Preferably, the structure support arrangement defines at least one support side along which the structure is supported in operation, and the post receiving formation is located adjacent to the at least one support side.

Preferably, the structure support arrangement further comprises one or more plates secured to the body member, in proximity of the post receiving formation, and adapted to prevent lateral movement of the support post in at least one transverse direction when the support post is received in the post receiving formation.

Preferably, the one or more plates comprise one plate secured to the body member to at least partially cover an opening of the post receiving formation so as to prevent the support post from laterally sliding out of the post receiving formation.

Preferably, the one or more plates comprise two plates secured to the body member, such that a gap between the two plates, when secured to the body member, is smaller than the opening of the post receiving formation.

Preferably, the one or more plates are at least partially embedded in the body member when secured to the body member.

Preferably, the one or more plates are removably secured to the body member.

Preferably, the one or more plates are provided with holes adapted to receive one or more fasteners in order to secure the one or more plates to the body member.

Preferably, the body member has threaded holes corresponding with the holes of the one or more plates.

Preferably, the one or more plates comprise one plate, the one plate being a pivotable latch adapted to pivot between an open position and a closed position, such that, in the open position, the one plate enables the support post to move in and out of the post receiving formation and in the closed position, the one plate prevents the support post from laterally moving out of the post receiving formation.

Preferably, the body member has an embedded pin about which the one plate is adapted to pivot.

Preferably, the one or more plates comprise one plate, the one plate being a slidable latch adapted to slide between an open position and a closed position, such that, in the open position, the one plate enables the support post to move in and out of the post receiving formation and in the closed position, the one plate prevents the support post from laterally moving out of the post receiving formation.

Preferably, the body member has a sliding cavity along which the one plate is adapted to slide.

Preferably, a shape of the post receiving formation conforms to a cross-sectional shape of the support post.

Preferably, the shape of the post receiving formation is rectangular.

Preferably, the structure support arrangement further comprises one or more dovetail formations defined on the body member and configured for sliding engagement with one or more dovetail formations on the further structure support arrangement in operation. The dovetail formations provide additional restriction against the displacement of the structure support arrangement in transverse directions.

Preferably, the structure support arrangement further comprises one or more pole receiving apertures defined on the body member. The one or more pole receiving apertures allow the structure support arrangement to be used as fence supports. Additionally, the one or more pole receiving apertures allow a lever to be inserted through the structure support arrangement, such that, a plurality of stacked structure support arrangements may be pivoted to receive the support post.

Preferably, the one or more pole receiving apertures are located towards an edge of the structure support arrangement.

Preferably, the body member is made of plastic.

Preferably, the body member is made using a technique selected from a group of technologies including injection moulding, rotary moulding and blow moulding.

Preferably, the body member is a hollow member. The hollow member is filled with a coagulable material. The coagulable material provides sufficient weight to the structure support arrangement.

Preferably, the structure support arrangement further comprises one or more handle formations defined on the body member and configured to facilitate stacking of the structure support arrangement with the further structure support arrangement in operation.

Preferably, the structure support arrangement further comprises a recess defined on the body member and configured to receive a bar that extends into a corresponding recess of another further structure support arrangement. The bar prevents displacement of stacks of the structure support arrangements.

In accordance with a second aspect of the invention, there is provided a strength enhancing structure for enhancing strength of a structure support arrangement, the strength enhancing structure comprising a main body having a first end and a second end; a first connection mechanism at the first end of the main body to connect to a first part of the structure support arrangement, the first connection mechanism being configured to support the main body via the first part of the structure support arrangement; and a second connection mechanism at the second end of the main body to connect to a second part of the structure support arrangement, the second connection mechanism being configured to support the second part of the structure support arrangement via the main body to enhance strength of the second part of the structure support arrangement.

It is an advantage of the present invention that the structure support arrangement, particularly, the second part of the structure support arrangement is provided with additional strength by connecting the first end of the main body of the strength enhancing structure to the first part of the structure support arrangement and connecting the second end of the main body of the strength enhancing structure to the second part of the structure support arrangement. This particularly improves the stability of the structure support arrangement when supporting heavier panels, banners and hoardings or in different weather conditions.

The first connection mechanism may further comprise a first connection plate extending from the first end of the main body and at least one connection bar extending from the first connection plate to be securely inserted to the first part of the structure support arrangement.

The at least one connection bar may further include two connection bars.

The first connection mechanism may further comprise a first clamping arrangement configured to clamp the first end to the first part of the structure support arrangement.

The first connection mechanism may further comprise a first snap fit arrangement having a first spring loaded chuck configured to receive the first end.

The first connection mechanism may further comprise a first connection plate extending from the first end of the main body and at least one first hole extending through the first connection plate.

The strength enhancing structure may further comprise at least one first fastener to securely connect the first connection mechanism to the first part of the structure support arrangement through the at least one first hole.

The second connection mechanism may further comprise a second connection plate extending from the second end of the main body and at least one second hole extending through the second connection plate.

The strength enhancing structure may further comprise at least one second fastener to securely connect the second connection mechanism to the second part of the structure support arrangement through the at least one second hole.

The strength enhancing structure may further comprise a cut out in the second connection plate.

The second connection mechanism may further comprise a second clamping arrangement configured to clamp the second end to the second part of the structure support arrangement.

The second connection mechanism may further comprise a second snap fit arrangement having a second spring loaded chuck configured to receive the second end.

In accordance with a third aspect of the invention, there is provided a support-weight, also referred to herein as a structure support arrangement.

The support-weight of the third aspect of the invention includes:

a body;

a post receiving formation defined by the body such that a hoarding panel support post to which a hoarding panel is securable is able to be directly received into the post receiving formation;

a nesting formation defined by the body such that, where the support-weight is nested with a further support-weight having a complementary nesting formation defined by the body of the further support-weight, lateral movement of the support-weight with respect to the nested further support-weight is inhibited.

Preferably, the panel support post is able to be directly received into the post receiving formation of each of the support-weight and a nested further support-weight.

Preferably, the panel support post is able to travel through the support-weight and the nested further support-weight.

Preferably, the post receiving formation is adapted to receive a panel support post having a rectangular cross-section.

Preferably, the post receiving formation is a rectangular shape such that a wider dimension of the post receiving formation is perpendicular to a near edge of the support-weight, the near edge being the edge of the support-weight nearest to the hoarding panel securable to the panel support post.

Preferably, the rectangular shape of the post receiving formation conforms to the rectangular cross-section of the panel support post which it is adapted to receive.

Preferably the support-weight includes a plate secured to the body, the plate being located proximate to the post receiving formation and adapted to prevent lateral movement of the panel support post when the post is received into the post receiving formation.

Preferably, the support-weight includes at least one plate having a tapered section such that a gap is formed between the at least one plate of the support-weight and the at least one plate of a nested further support-weight.

Preferably, the support-weight includes two plates, each plate having a tapered section.

Preferably, the two tapered plates are contiguous at their respective narrowest sections.

Preferably, the gap formed between the plates of a support-weight and a nested further support-weight is sized such that a fastener may be inserted through the panel and the gap and into the panel support post to secure the support-weight to the panel and the panel support post.

Preferably, the support-weight in plan view has a wider central section such that the width of the central section of the support-weight is greater than the width of the weight at a near end, and greater than the width of the weight at a far end of the weight.

Preferably, the support-weight is octagonal in plan view.

Preferably, the post receiving portion is located towards a near end of the weight.

Preferably, the support-weight includes at least one recesses located towards a far end of the support-weight.

Preferably, the support-weight includes a pair of adjacent cylindrical recesses each adapted to receive a cylindrical post of a fencing structure.

In accordance with a fourth aspect of the invention, there is provided a strengthening post, also referred to herein as a strength enhancing structure.

The strengthening post in accordance with the fourth aspect of the invention includes:

a main body;

a first mechanism located at a first end of main body, the first mechanism being adapted to securely engage with at least one of a plurality of nestable support-weights; and a second mechanism located at a second end of the main body, the second mechanism being adapted to fasten to a panel support post.

Preferably, the first mechanism is able to insert into at least the uppermost support-weight the plurality of nestable support-weights.

Preferably, the first mechanism is able to insert into at least the uppermost two support-weights of the plurality of nestable support-weights.

Preferably, the first mechanism includes a connection plate extending from a first end of the main body and at least one bar extending from the connection plate.

Preferably, the at least one bar is able to insert into a complementary shaped recess in each of the at least two uppermost support-weights of the plurality of nestable support-weights.

Preferably, the first mechanism includes a connection plate and two bars, each bar able to insert into a complementary recess in each of the at least the uppermost support-weights of the plurality of nestable support-weights.

Preferably, the second mechanism includes a second connection plate extending from a second end of the main body and at least one hole extending through the second connection plate.

Preferably, the hole extending through the second connection plate may be adapted to receive a fastener through the at least one hole to fasten the second end of the main body to the panel support post.

Preferably, the strengthening post is able to triangulate the plurality of nestable support-weights and the panel support post.

Preferably, the triangulation of the plurality of nestable support-weights and the panel support post by the strengthening post increases the stability of a system consisting of the plurality of nestable support-weights, the panel support post and a panel secured to the panel support post by raising the fulcrum point of the system.

Preferably main body includes a bend located towards the second end of the main body.

In accordance with a fifth aspect of the invention, there is provided a hoarding panel support system including a plurality of nestable support-weights as described above and the strengthening post as described above.

Preferably, the hoarding panel support system is able to be triangulated with a panel support post as described above in relation to the fourth aspect of the invention.

In accordance with a sixth aspect of the invention, there is provided a method of installing a hoarding, the hoarding including a hoarding panel, a panel support post, a plurality of nestable support-weights and a strengthening post, the method including the steps of:

stacking the plurality of support-weights one on top of the other;

inserting the panel support post into the post receiving formation of each of the stacked support-weights;

securely engaging the strengthening post with at least one of the plurality of nestable support-weights;

fastening the strengthening post to the panel support post; and securing the hoarding panel to the panel support post.

Preferably, the hoarding panel is securable to the panel support post by securing means such as screws.

Preferably, the strengthening post is able to be fastened to the panel support post by fastening means such as screws In accordance with a seventh aspect of the invention, there is provided a hoarding installation including a hoarding panel, a panel support post, a plurality of nestable support-weights, a strengthening post, wherein the hoarding installation is installed in accordance with the method of the sixth aspect of the invention.

In accordance with an eighth aspect of the invention, there is provided a method of installing a fencing structure using a plurality of support-weights each having a first fencing post recess and a second fencing post recess adjacent to the first fencing post recess, the fencing structure including a plurality of fencing panels and each fencing panel including a fencing post extending downwardly from the fencing panel, the method including the steps of:

placing the plurality of support-weights on a surface; and inserting fencing posts of two fencing panels into one support-weight such that the one support-weight receives a post of a first fencing panel into its first fencing post recess and a post of a second fencing panel into its second adjacent fencing post recess.

Other aspects of the invention are also disclosed.

It will be apparent to the skilled person in the art that one or more of the abovementioned aspects of the invention provide one or more of the following advantages over the prior art:

The post receiving formation defined by the body of the support-weight can directly receive a hoarding panel support post to which a hoarding panel is securable. This provides the advantage of avoiding any separate connector, extension, or other means to receive the panel support post which is outside the form of the weight and which may enlarge the footprint made by the combination of the weight and hoarding panel support post. Space for workers to operate behind a hoarding panel may be limited, so a small footprint is of great importance.

A small footprint of the support-weight also results from: (i) the strengthening post being directly receivable by the support-weight; and/or (ii) the shape of the support-weight in a non-rectangular form with a wider central section (in plan view) permitting the mass of a stack of nestable support-weights to be located closer towards the hoarding panel so the weight extend less into the working space behind the hoarding than would be the case for comparable rectangular plan view shaped support-weight; and/or the nestability of the support-weights themselves.

The invention has fewer interoperating parts than other systems in the prior art. For a hoarding installation the invention requires only three components separate from the hoarding panel, and for a fencing installation the invention requires only one component separate from the fencing panel.

The invention provides for easy stacking of the support-weights using handle formations so that a support-weight can be picked up and put down without trapping the operator's fingers. Angled corners also allow the weights to be safely stacked on pallets, where abutting stacks of weights would again inhibit the operator's ability to safely handle the weights. The weights are also adapted to be a convenient size and weight for lifting. Other advantages due to the size and shape of the weights are gained in that fewer weights (compared with prior art systems) are required to be used in conjunction with the strengthening post to achieve certification of relevant industry standards. See, for example, Australian Standards AS4687-2007—"Temporary Fencing and Hoardings" and AS1170.2-2011—"Structural design actions—Wind actions".

Use of the strengthening support post raises the fulcrum point of a hoarding installation so that it is higher than it would be without the use of the support post. This means that collapsing of the hoarding installation is inhibited when subject to forces against a hoarding panel.

The orientation of a panel support post having a rectangular cross-section such that the wider dimension of the panel support post is perpendicular to the near edge of the support-weight. This orientation is different to the prior art in which has the wider dimension of the panel support post run parallel with the near edge of the support-weight. This provides substantial strength gains, as the forces on the panel support post are concentrated about the deep axis of the post (for example, in a commonly available shaped post, approximately 90 mm deep) instead of the shallow axis of the stud (for example, in a commonly available shaped post, approximately 45 mm deep).

The invention is able to used with panel support posts of a standard size (for example, a "2×4" which is approximately 40 mm×90 mm) and meet the relevant industry standards. The invention is able to be used with standard grade panel support posts (for example, a MPG10 grade timber stud).

Where a system is not braced (for example, by attachment to a wall or ceiling) lateral, post installation movement or "snaking" could occur. To avoid this, the invention contemplates use of a horizontal bar received into a complementary recess in the uppermost support-weight of a hoarding installation. The horizontal bar may also be affixed to one or more panel support posts (for example, by means of affixing means (such as a screw) between the panel support post and the horizontal bar and/or the hoarding panel.

The invention provides the user the ability to install a pre-certified and structural engineer approved counter-weight solution. The user is able to follow a simple process and ensure that the panels are secure, and the system is safe.

Once a hoarding installation is complete, the weights cannot be removed without first removing the panels (which are the area of risk if impacted). By comparison in the prior art which uses an upright stand, the weights can be added and removed without removing the panel and this is not tamperproof, but since the panels of a hoarding installation in accordance with invention may screwed into the panel support post (in the space between the plates), once the panel is secured to the panel support posts, the support-weights cannot be removed until after the screws affixing the hoarding are removed, and (by extension) the hoarding panel itself.

BRIEF DESCRIPTION OF THE DRAWINGS

Notwithstanding any other forms which may fall within the scope of the present invention, preferred embodiments of the invention will now be described, by way of example only, with reference to the accompanying drawings in which.

DETAILED DESCRIPTION

Figure 1:
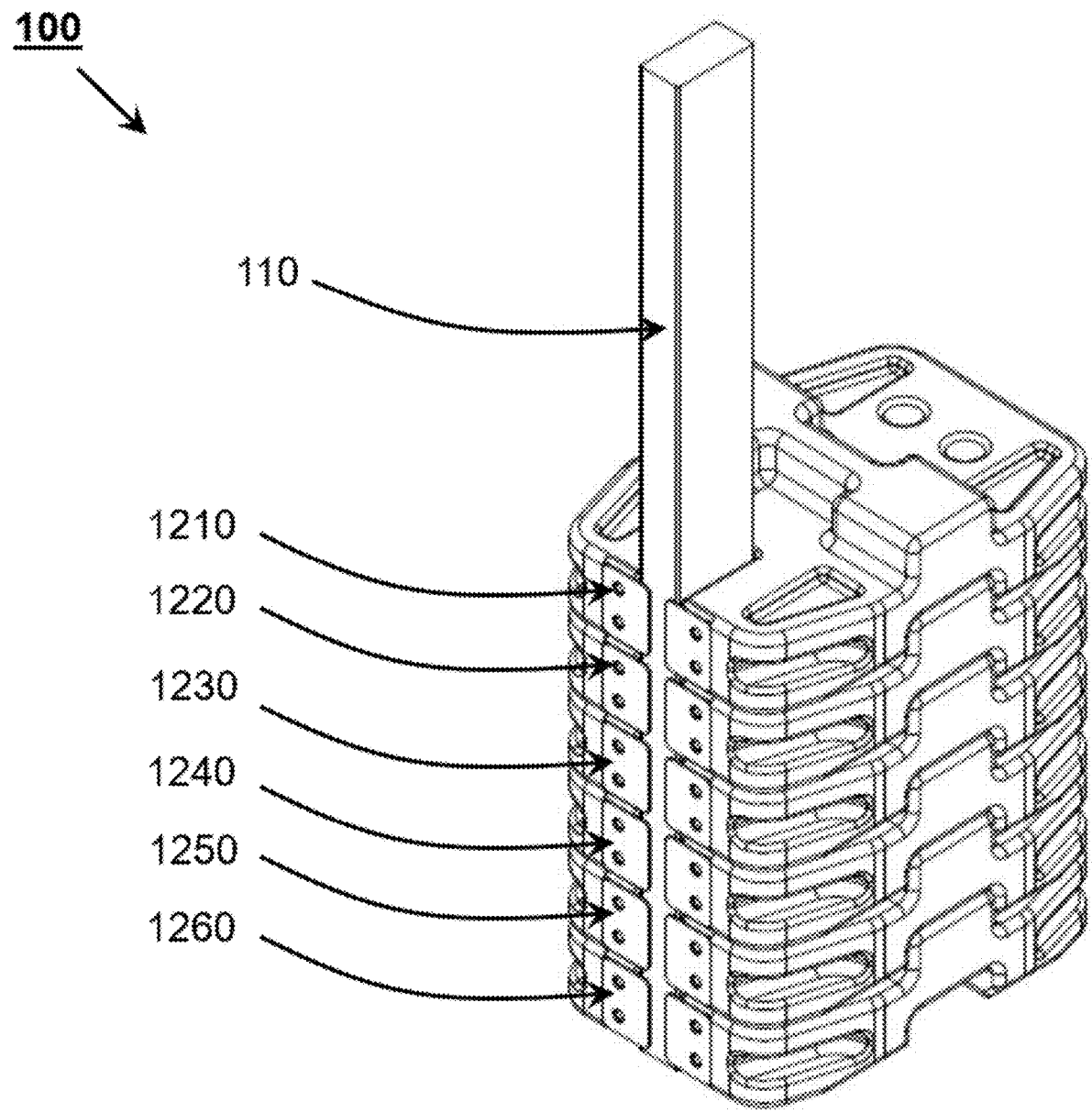
FIG. 1 illustrates a plurality of structure support arrangements (also called support-weights) stacked along a support post in accordance with a preferred embodiment of the present invention.

It should be noted in the following description that like or the same reference numerals in different embodiments denote the same or similar features.

FIG. 1 illustrates a plurality of structure support arrangements 1210, 1220 1230, 1240, 1250, and 1260 stacked along a support post 110 in accordance with a preferred embodiment 100 of the present invention. At a construction site or shop renovation site, multiple stacks of the structure support arrangements are placed along the boundary of the site. One or more hoardings or panels are fixed to the support posts 110. This way, a wall or a fence is formed along the boundary of the site to for example prevent pedestrians from entering into this site. A structure support arrangement is also herein referred to as a support-weight.

Figure 2:
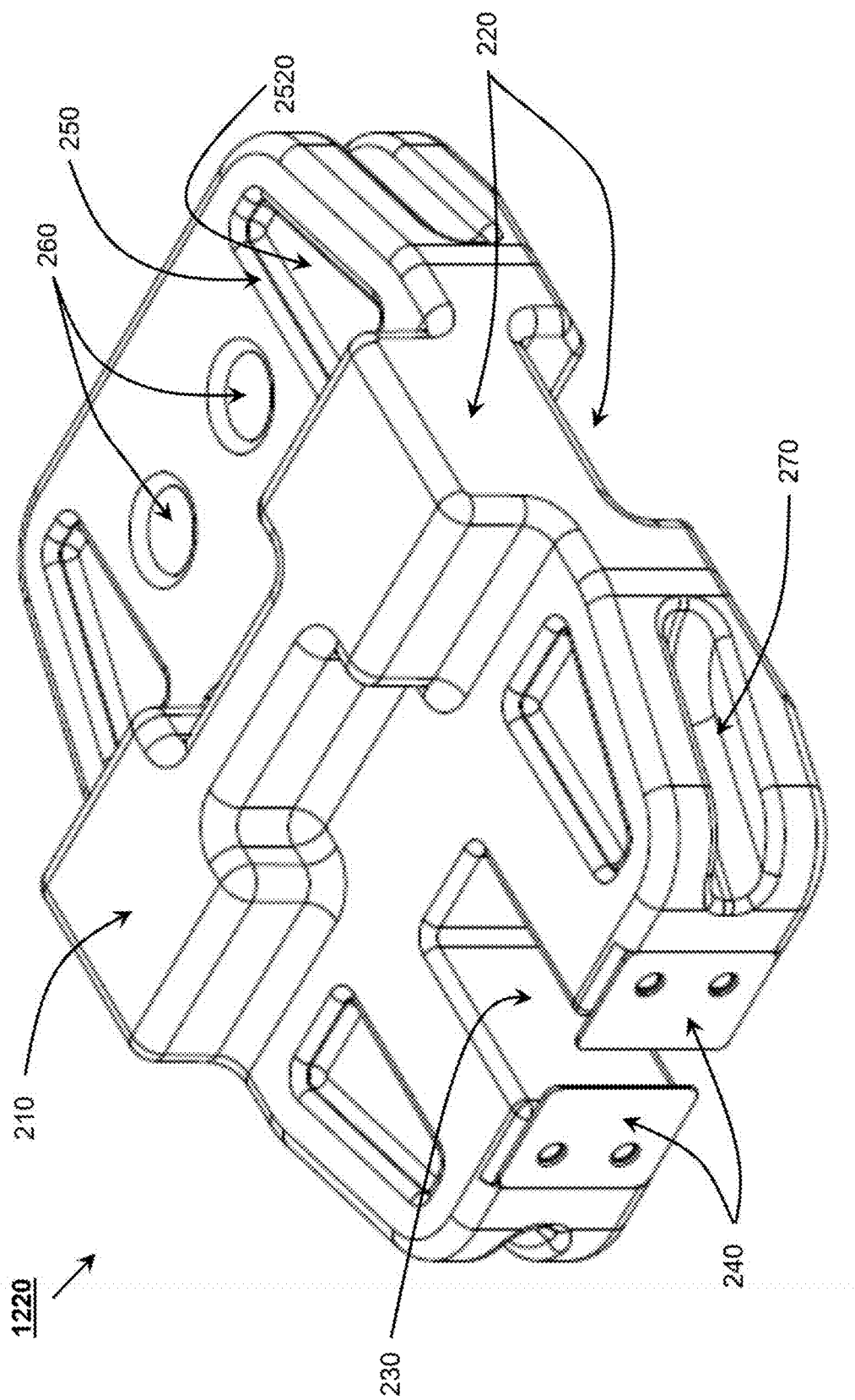
FIG. 2 illustrates a top perspective view of a structure support arrangement in accordance with a preferred embodiment of the present invention.

FIG. 2, illustrates a top perspective view of a structure support arrangement 1220 of the plurality of structure support arrangements 1210 to 1260, in accordance with a preferred embodiment of the present invention. As shown in FIG. 2, the structure support arrangement 1220 comprises a body member 210. In one embodiment of the invention, the body member 210 is made of plastic. Further, in one embodiment, body member 210 is made using a technique selected from a group of technologies including injection moulding, rotary moulding and blow moulding.

Further, the structure support arrangement 1220 includes a nesting formation 220 defined on the body member 210. The nesting formation 220 is configured to prevent lateral movement of the structure support arrangement 1220 in at least one transverse direction when the structure support arrangement 1220 is nested with a further structure support arrangement, particularly, an adjacent similar structure support arrangement 1210 or 1230.

The transverse direction is a direction defined by x and y directions (as indicated by the x and y arrows in FIG. 3) and is perpendicular to the longitudinal direction of the support post 110 in operation. For example, a transverse direction that is substantially in x and y plane can be defined by a linear combination of x and y directions.

Figure 3:
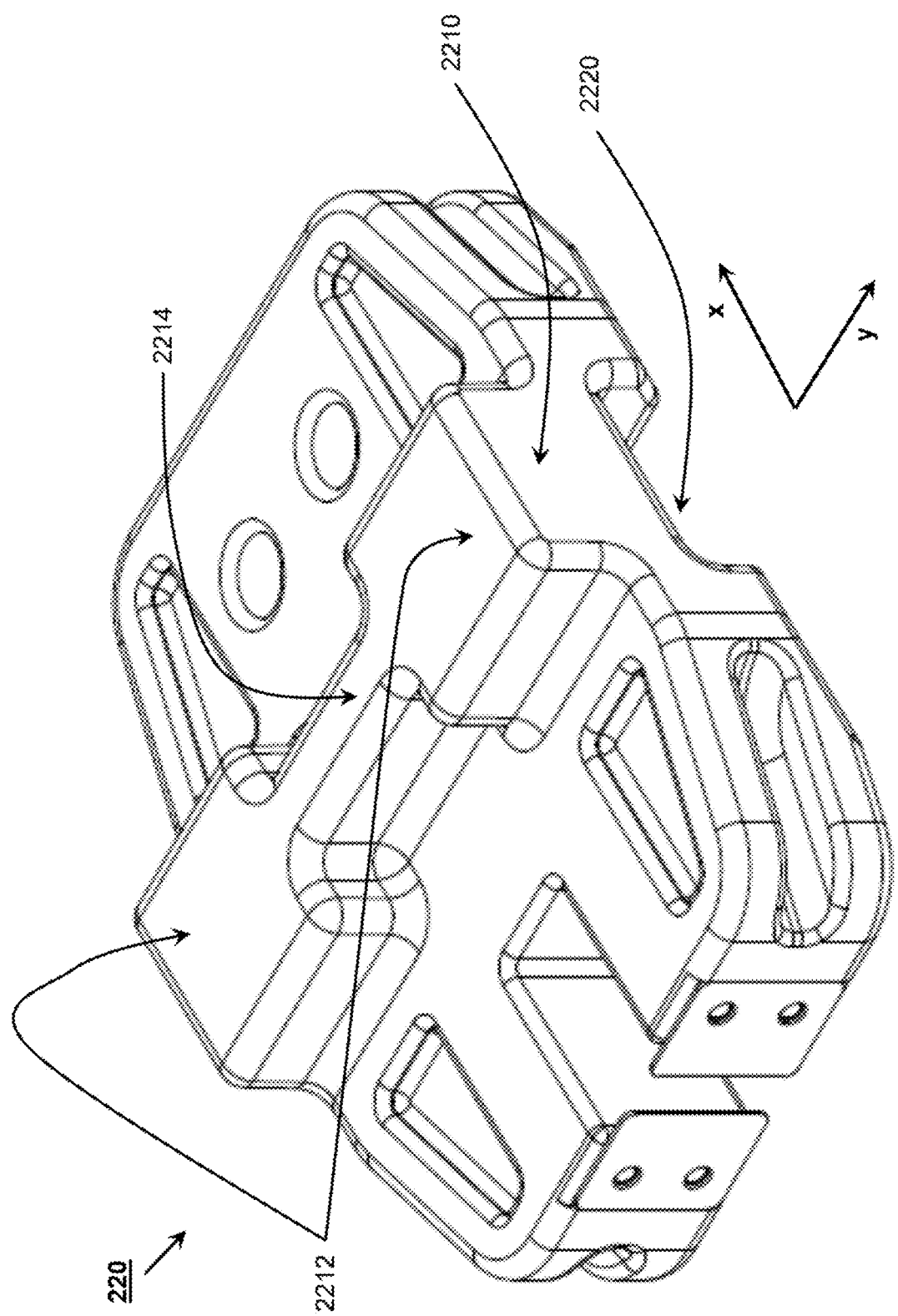
FIG. 3 illustrates a nesting formation in accordance with another preferred embodiment of the present invention.

FIG. 3 illustrates the nesting formation 220 in accordance with a preferred embodiment of the present invention. As shown in FIG. 3, the nesting formation 220 comprises an I-shaped projection 2210 and an I-shaped cavity 2220. The I-shaped projection 2210 has one or more projection heads 2212 and a projection neck 2214 connecting therebetween.

Figure 4:
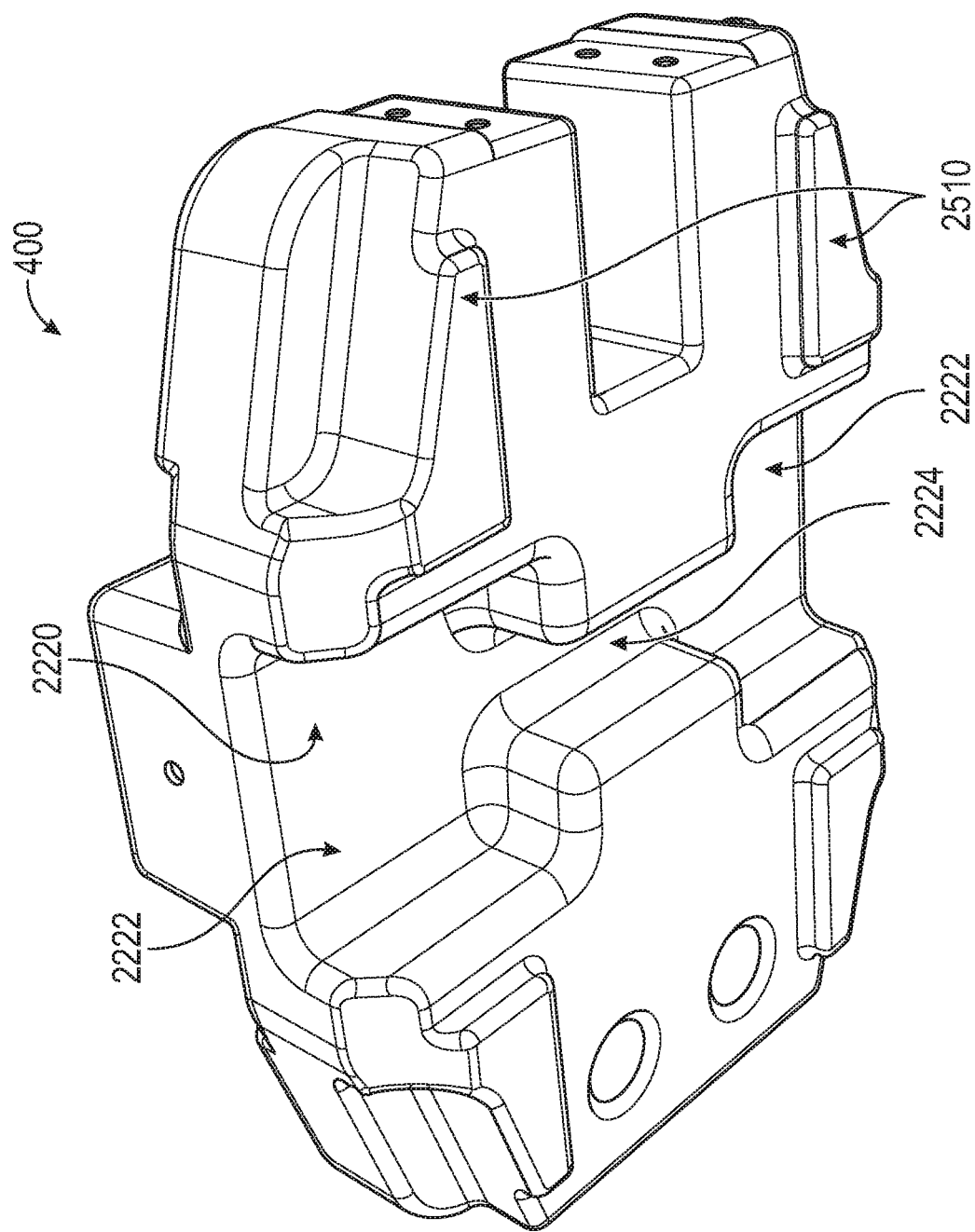
FIG. 4 illustrates a bottom perspective view of the structure support arrangement in accordance with a preferred embodiment of the present invention.

FIG. 4 illustrates a bottom perspective view of the structure support arrangement 1220 in accordance with a preferred embodiment 400 of the present invention. As shown in FIG. 4, the I-shaped cavity 2220 has one or more cavity heads 2222 and a cavity neck 2224.

If the structure support arrangement 1220 is nested with the adjacent similar structure support arrangement 1210, the two projection heads 2212 of the structure support arrangement 1220 mate with the two cavity heads 2222 of the adjacent similar structure support arrangement 1210. Further, the projection neck 2214 of the structure support arrangement 1220 mates with the cavity neck 2224 of the adjacent similar structure support arrangement 1210. The adjacent similar structure support arrangement 1210 is installed on the top of the structure support arrangement 1220. As a result, the lateral movement of the structure support arrangements 1210 and 1220 relative to each other in at least one transverse direction can be prevented.

On the other hand, as shown in FIG. 1, the one or more cavity heads 2222 and cavity neck 2224 of the structure support arrangement 1220 mate with the corresponding one or more projection heads 2212 and projection neck 2214 of the structure support arrangement 1230, which is installed under the structure support arrangement 1220. As a result, the lateral movement of the structure support arrangements 1220 and 1230 relative to each other in at least one transverse direction can be prevented.

Figure 5:
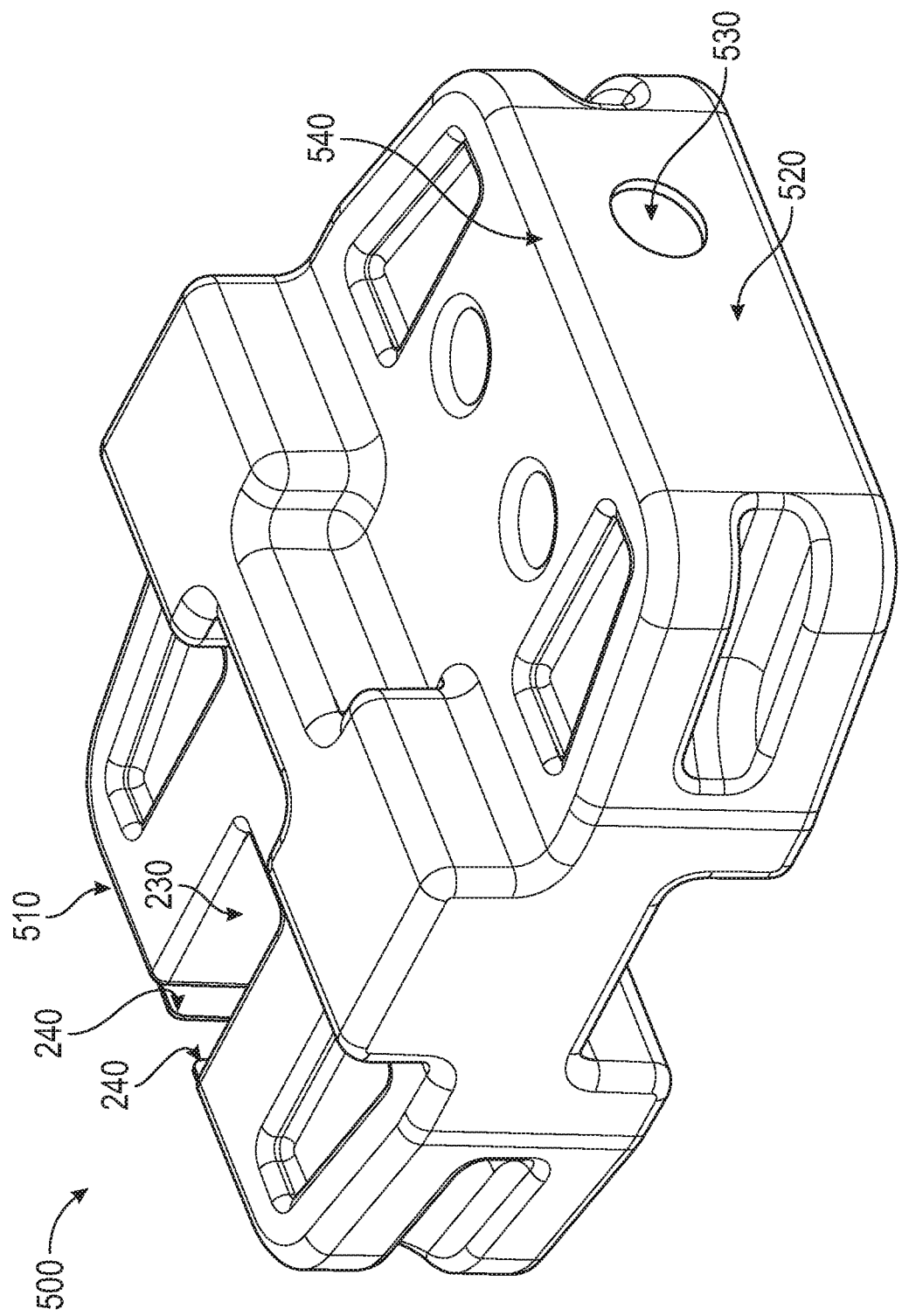
FIG. 5 illustrates the structure support arrangement in accordance with another preferred embodiment of the present invention.

Returning now to FIG. 2, the structure support arrangement 1220 further comprises a post receiving formation 230 defined on the body member 210. The post receiving formation 230 is configured for receiving the support post 110. In one embodiment, the post receiving formation 230 is any one or more selected from an aperture and a recess. The post receiving formation 230 includes an opening formed on a side (particularly, the support side 510, as shown in FIG. 5) of the structure support arrangement 1220. Further, in one embodiment, a shape of the post receiving formation 230 conforms to a cross-sectional shape of the support post 110 in order for the support post 110 to fit into the post receiving formation 230. In another embodiment, the shape of the post receiving formation is rectangular regardless of the cross-sectional shape of the support post 110.

In one embodiment, the structure support arrangement 1220 comprises one or more plates (i.e., lip plates) 240 secured to the body member 210, in proximity of the post receiving formation 230. Further, the one or more lip plates 240 are adapted to prevent lateral movement of the support post 110 in at least one transverse direction when the support post 110 is received in the post receiving formation 230.

In one embodiment, one lip plate is secured to the body member 210 to entirely or partially cover the opening of the post receiving formation 230 so as to prevent the support post 110 from laterally sliding out of the post receiving formation 230 in at least one transverse direction.

In one embodiment in which two lip plates are used, a gap between the two lip plates 240, when secured to the body member 210, is smaller than the opening of the post receiving formation 230, as shown in FIG. 2. Thus, when the support post 110 is received in the post receiving formation 230, the one or more lip plates prevent the support post 110 from laterally sliding out of the post receiving formation 230 in at least one transverse direction.

In one embodiment of the invention, the one or more lip plates 240 are removably secured to the body member 210, such as by means of one or more fasteners. Further, the one or more lip plates 240 are provided with holes adapted to receive the one or more fasteners in order to secure the one or more lip plates 240 to the body member 210. Accordingly, the body member 210 has threaded holes corresponding with the holes of the one or more lip plates 240.

In another embodiment, the one or more lip plates 240 are at least partially embedded in the body member 210 when secured to the body member 210.

In another embodiment, the one lip plate 240 is a pivotable latch adapted to pivot between an open position and a closed position. In the open position, the lip plate 240 enables the support post 110 to move in and out of the post receiving formation 230. In the closed position, the one lip plate 240 prevents the support post 110 from laterally moving out of the post receiving formation 230 in at least one transverse direction. Accordingly, the body member 210 has an embedded pin about which the one lip plate 240 is adapted to pivot. In yet another embodiment, the one lip plate 240 is a slidable latch adapted to slide between the open position and the closed position. Accordingly, the body member 210 has a sliding cavity along which the one lip plate 240 is adapted to slide.

In one embodiment, the structure support arrangement 1220 further comprises one or more dovetail formations 250 defined on the body member 210. Further, the one or more dovetail formations 250 are configured for sliding engagement with one or more dovetail formations on the adjacent similar structure support arrangement 1210 in operation. In one embodiment, the one or more dovetail formations 250 comprise respective one or more dovetail projections 2510 (shown in FIG. 4) and respective one or more dovetail cavities 2520 (shown in FIG. 2). In sliding engagement, the one or more dovetail projections of the adjacent similar structure support arrangement 1210 mate with the one or more dovetail cavities 2520 of the structure support arrangement 1220. The one or more dovetail formations 250 provide additional restriction to the structure support arrangement 1220 against lateral movements in at least one transverse direction.

In one embodiment, the structure support arrangement 1220 further comprises one or more pole receiving apertures 260 defined on the body member 210. In one embodiment, the one or more pole receiving apertures 260 are configured to receive poles. The pole can be part of a structure such as a web with poles at the edges of the web. The pole at one edge of the web is received into the pole receiving aperture 260 of the structure support arrangement 1220, and the pole at another edge of the web is received into the pole receiving aperture of another structure support arrangement. When the web is erected, the two structure support arrangements servers as the bases of the web and keep the web upright.

Figure 8:
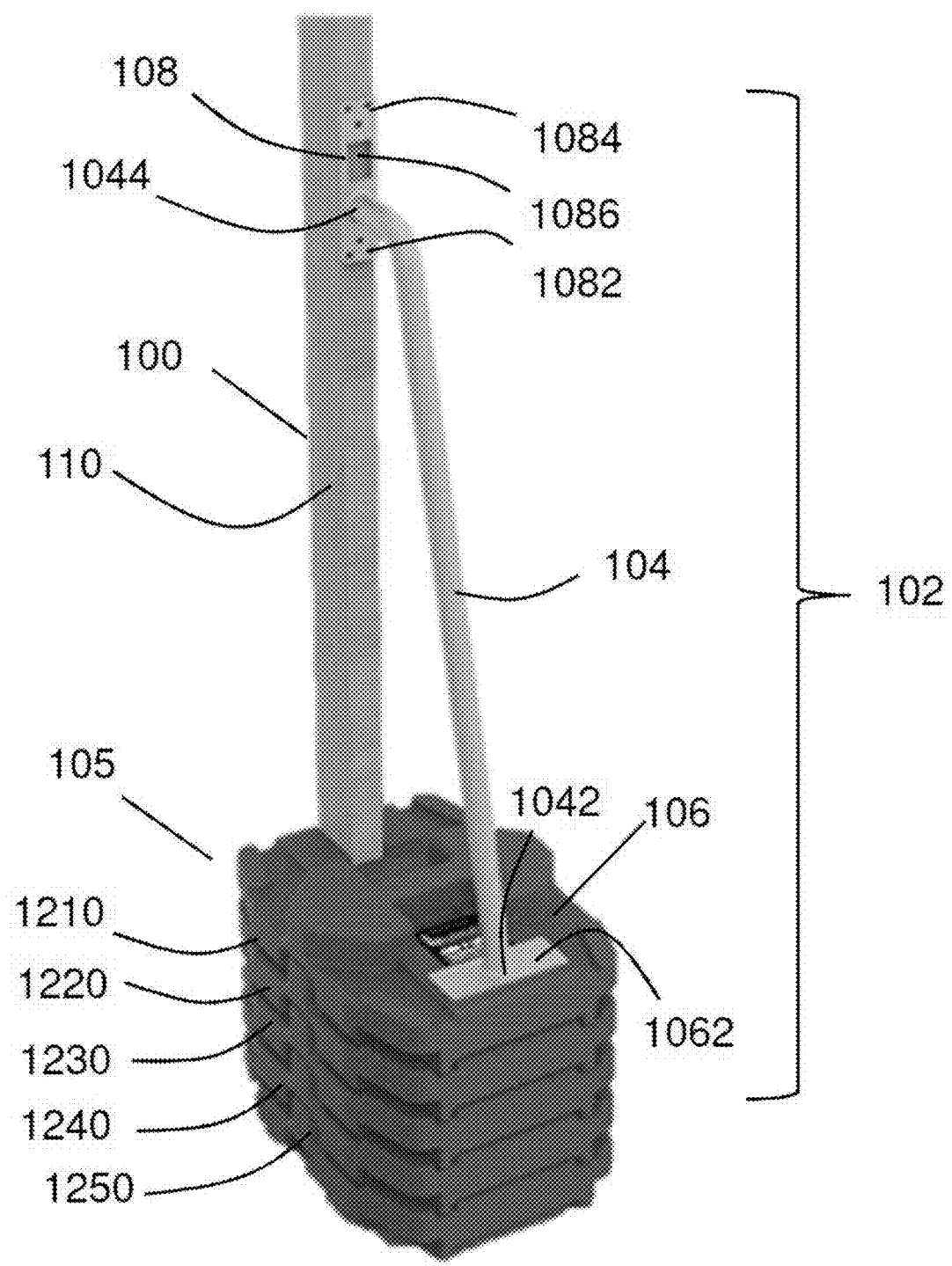
FIG. 8 illustrates a front perspective view of a plurality of structure support arrangements stacked along a support post and with a support post attached therebetween in accordance with a preferred embodiment of the present invention.
Figure 9:
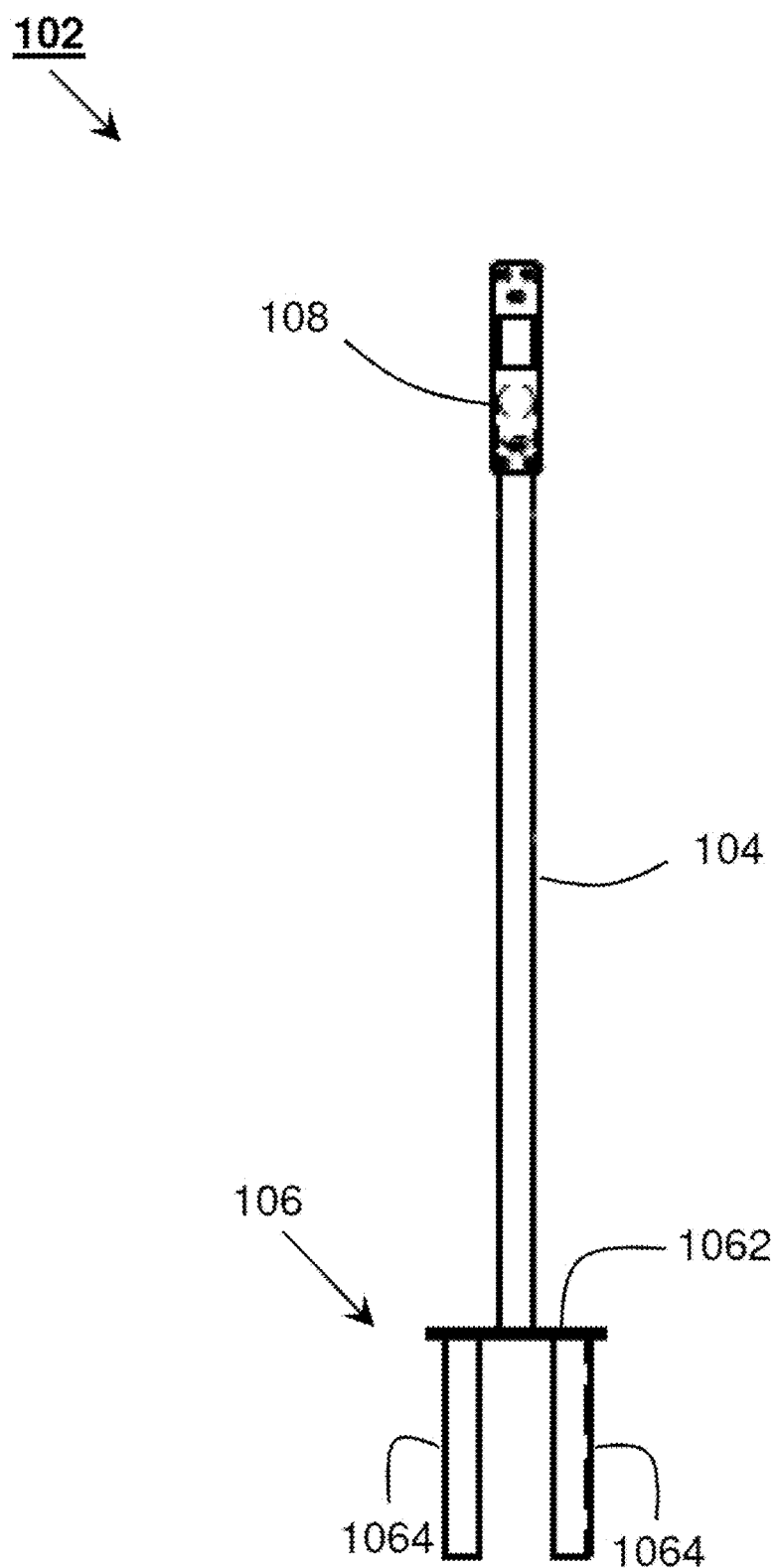
FIG. 9 is a front elevation of the support post of FIG. 8.

Referring to FIGS. 8 and 9 there is illustrated an embodiment of the strength enhancing structure 102 in accordance with an embodiment of the present invention. The strength enhancing structure 102 comprises a main body 104 having a first end 1042 and a second end 1044. The main body 104 may have for example a circular cross-section, a rectangular cross-section or a trapezoidal cross-section. In one embodiment, the main body 104 has a straight profile throughout the length of the main body 104. In another embodiment, the main body 104 may have one or more bends at a predetermined angle and at a predetermined distance from the first end 1042 or the second end 1044. In one embodiment, the main body 104 has an L-shaped profile. Also, the main body 104 may have an arc-like profile. The arcs and other bends are provided to the main body 104 in order to provide additional rigidity to the main body 104 against buckling or other failures due to localized stress concentration.

Further, the main body 104 may be made of, but not limited to, a wood, metal, an alloy or a rigid material having sufficient compressive and/or tensile strength, depending upon the material used for making the first part 105 and the second part 110 of the structure support arrangement 100. Also, the main body 104 may be a solid or a hollow component. Making the main body 104 hollow provides weight reduction and avoid material wastage. In that manner, it is envisaged that the material chosen for the hollow main body 104 will have sufficient strength to withstand the stresses generated during operation.

A first connection mechanism 106 is provided at the first end 1042 of the main body 104. The first connection mechanism 106 is configured to connect the first end 1042 of the main body 104 of the strength enhancing structure 102 to the body member 210 of the counterweight 1210, i.e., the first part 105 of the structure support arrangement 100. In various embodiments, first connection mechanism 106 comprises a first connection plate 1062 extending from the first end 1042 of the main body 104. Also, at least one connection bar 1064 extends from the first connection plate 1062. In one embodiment, the at least one connection bar 1064 includes two connection bars 1064. The at least one connection bar 1064 is configured to be securely inserted to the cavity 260 of the body member 210. It is envisaged here that a dovetail joint may be provided between the at least one connection bar 1064 and the cavity 260, to ensure that the at least one connection bar 1064 is secured within the cavity 260. Further, it is envisaged that the cross section of the at least one connection bar 1064 is adapted to conform to the shape of the cavity 260. This secures the first connection mechanism 106 and thereby, the first end 1042 of the main body 104, in the body member 210.

In various other embodiments, the first connection mechanism 106 includes a first clamping arrangement configured to clamp the first end 1042 to the first part (or the counterweigh 1210 here). In yet another embodiment, the first connection mechanism 106 includes a first snap fit arrangement having a first spring loaded chuck configured to receive the first end 1042. In one embodiment, the first connection plate 1062 of the first connection mechanism 106 has at least one first hole. The at least one first hole may be internally threaded. Also, the at least one first hole is configured to receive the at least one first fastener and prevent the movement of the first connection plate 1062 and thereby the movement of the strength enhancing structure 102, with respect to the first part 105 and the second part 110. In various embodiments, the at least one first fastener may include any one of a screw, a bolt, a nut and bolt combination, a stud and many other variations as would be appreciated by a skilled addressee.

The strength enhancing structure 102 also includes a second connection mechanism 108 at the second end 1044 of the main body 104. The second connection mechanism 108 is configured to connect the second end 1044 of the main body 104 to the second part 110 (or the support post 110) of the structure support arrangement 100. In various embodiments, the second connection mechanism 108 further comprises a second connection plate 1082 extending from the second end 1042 of the main body 104. And the second connection plate 1082 has at least one second hole 1084 extending through the second connection plate 1082. The second connection mechanism 108 also includes at least one second fastener. In various embodiments, the at least one second fastener may include any one of a screw, a bolt, a nut and bolt combination, a stud and many other variations as would be appreciated by a skilled addressee.

The at least one second hole is configured to receive the at least one second fastener to securely connect the second connection mechanism 108 to the second part 110 (or the support post 110) of the structure support arrangement 100 through the at least one second hole 1084. In various other embodiments, the second connection mechanism 108 includes a second clamping arrangement configured to clamp the second end 1044 to the second part 110 of the structure support arrangement 100. In yet another embodiment, the second connection mechanism 108 embodies a second snap fit arrangement having a second spring loaded chuck configured to receive the second end 1044. Also, a cut-out 1086 is provided in the second connection plate 1082.

The first connection mechanism 106 and the second connection mechanism 108 are adapted to prevent motion of the strength enhancing structure 102 with respect to the first part 105 and the second part 110 of the structure support arrangement 100. The strength enhancing structure 102 is adapted to provide additional strength to the second part 110 (or the support post 110) via the main body 104.

In one embodiment, the strength enhancing structure 102 is removably attached to the body member 210 and the support post 110. The at least one connection bar 1064 of the first connection mechanism 106 may form detachable link with the cavity 260 having a press-fit locking and unlocking mechanism. And the second connection mechanism 108 may be detached from the support post 110 by unfastening the at least one second fastener on the second connection plate 1082.

As can be seen from the above description, the second part 110 of the structure support arrangement 100 is provided with additional strength by connecting the first end 1042 of the main body 104 of the strength enhancing structure 102 to the first part 1020 of the structure support arrangement 100 and connecting the second end 1044 of the main body 104 of the strength enhancing structure 102 to the second part 110 of the structure support arrangement 100. This way, the strength enhancing structure 102 increases the strength of the support post 110 and the stability of the structure support arrangement 100 when supporting heavier panels or hoardings fixed to the second post 110 and in different weather conditions.

It should also be noted that the structure support arrangement 100 described in the present disclosure is just an example of a structure support arrangement the strength of which the strength enhancing structure 102 can be used to enhance and is not limited to the configuration described in the present disclosure. That is, the structure support arrangement 100 can be configured in other ways. For example, the structure support arrangement 100 can simply include a base (i.e., the first part) and a support post (i.e., the second part) extending from the base to support a hoarding or a panel.

In one embodiment, the structure support arrangement 1220 further comprises one or more handle formations 270 defined on the body member 210. Further, the one or more handle formations 270 are configured to facilitate stacking of the structure support arrangement 1220 with the adjacent similar structure support arrangement 1210 or 1230 in operation. FIG. 5 illustrates the structure support arrangement 1220 in accordance with another preferred embodiment 500 of the present invention. As shown in FIG. 5, the structure support arrangement 1220 defines at least one support side 510 and at least one non-support side 520. Further, the structure is supported along the at least one support side 510 in operation. Also, the post receiving formation 230 is located adjacent to the at least one support side 510.

Also, the one or more pole receiving apertures 260 are located towards an edge 540 of the structure support arrangement 1210. In one embodiment, the edge 540 is located at the at least one non-support side 520. Also, in one embodiment, the body member 210 is a hollow member. The hollow member 210 is filled with a coagulable material, such as cement. The coagulable material provides a sufficient weight to the structure support arrangement. This provides the structure support arrangement with further stability. A filling aperture 530 is provided at the hollow member 210 at the at least one non-support side 520. The coagulable material is filled into the body member 210 through the filling aperture 530.

As shown in FIG. 1, multiple structure support arrangements 1210 to 1260 are stacked to form a stack of structure support arrangements 1210 to 1260. Multiple stacks of structure support arrangements are placed along the boundary of a site, for example, a construction site or a shop renovation site. The structures, for example, hoardings or panels, are fixed to the support posts 110. Thus, a wall or fence along the boundary of the site is formed to for example prevent pedestrians from entering into this site.

However, due to external forces caused by for example storms, the multiple stacks of structure support arrangements may be displaced. That is, the multiple stacks of structure support arrangements are no longer positioned along the boundary of the site, and the structures fixed to the support posts 110 appear to be like a "snake" when viewed from top. In an extreme case, this may cause the structures to fall off the support posts 110 and damage pedestrians nearby or workers working at the site.

Figure 6:
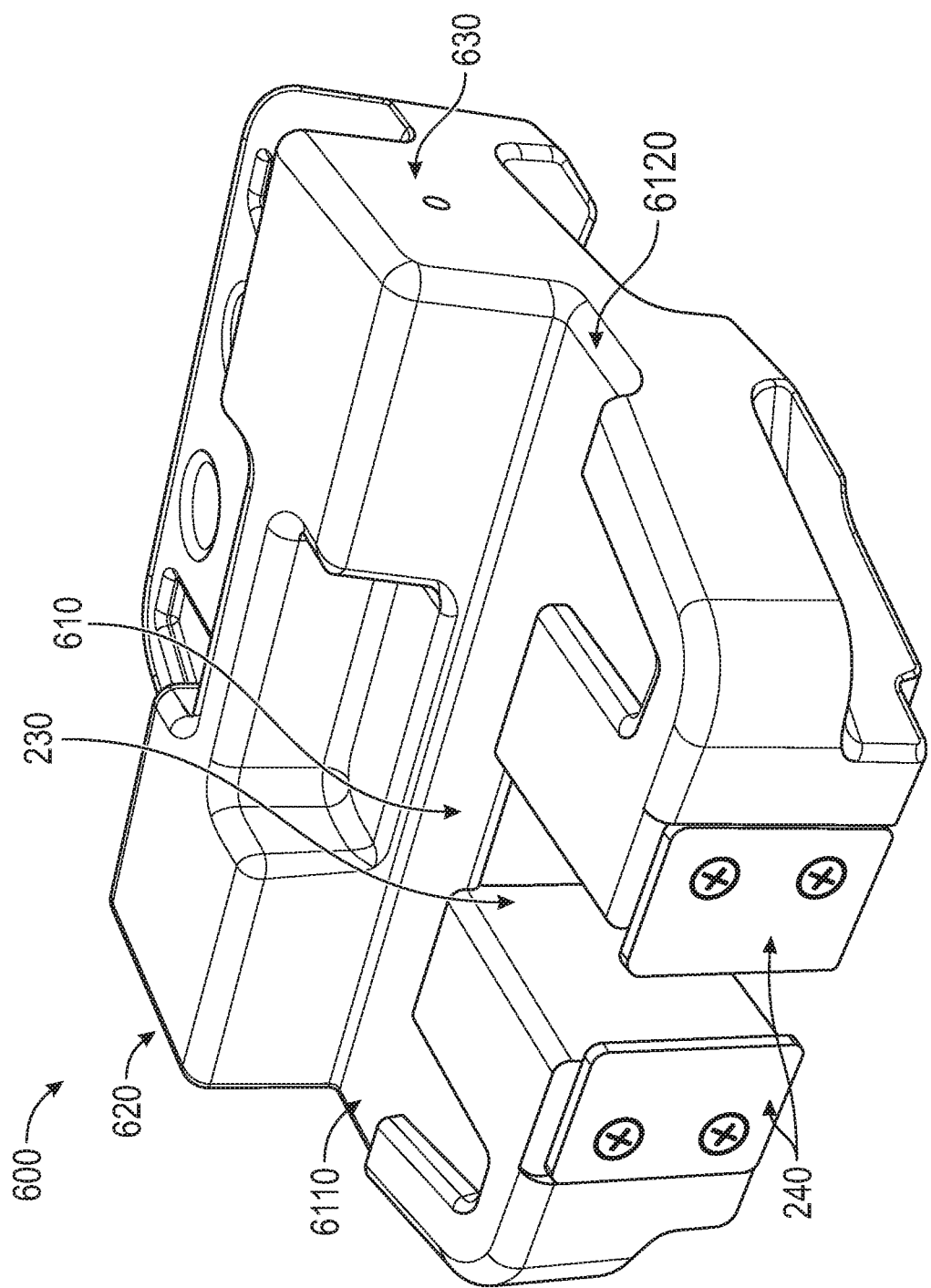
FIG. 6 illustrates a structure support arrangement in accordance with yet another preferred embodiment of the present invention.

FIG. 6 illustrates a structure support arrangement 1220 in accordance with yet another preferred embodiment 600 of the present invention. As shown in FIG. 6, the structure support arrangement 1220 further comprises a recess 610 defined on the body member 210. The recess 610 is provided along an entire width of the body member 210 with open ends 6110 and 6120 at two sides 620 and 630 of the structure support arrangement 1220, respectively. The recess 610 is configured to receive a horizontal bar 730 that extends to a further structure support arrangement, particularly, into the corresponding recess of a further structure support arrangement (shown in FIG. 7).

Figure 7:
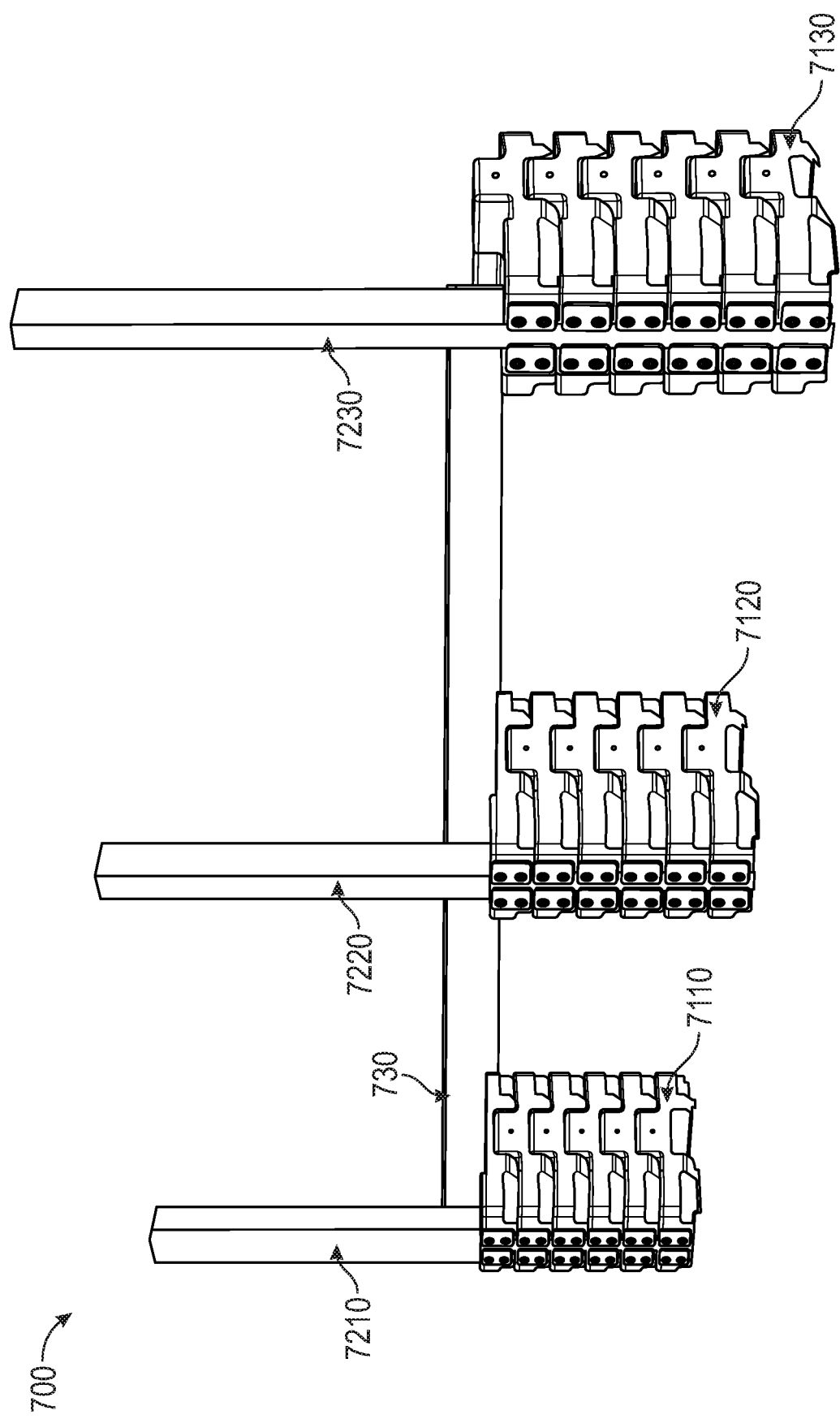
FIG. 7 illustrates a use of the structure support arrangement in stacks of structure supporting arrangements in accordance with an embodiment of the present invention.

FIG. 7 illustrates a plurality of structure support arrangement stacks 7110, 7120 and 7130. The stacks 7110 to 7130 are placed along a boundary of a site. A horizontal bar 730 is placed in the recesses 610 of the top structure support arrangement of each stack 7110 to 7130. The horizontal bar 730 connects the plurality of structure support arrangement stacks 7110, 7120 and 7130, and keep the plurality of structure support arrangement stacks 7110, 7120 and 7130 along the boundary of the site. The structures are fixed to support posts 7210, 7220 and 7230.

If an external force is applied to the structures, the horizontal bar 730 in the recesses 610 of the plurality of structure support arrangement stacks 7110, 7120 and 7130 effectively prevents the displacement of the plurality of structure support arrangement stacks 7110, 7120 and 7130, which dramatically reduces the possibility of the falling of the structures from the support posts 7210, 7220 and 7230. This improves the safety at the site.

The structure support arrangement 1210 to 1260 as described above offers a number of advantages. First, they are easy to manufacture and ship. The design of the body member provides sufficient prevention against displacement in transverse directions. The structure support arrangement allows easy support to structures without making any temporary or permanent indentations on the ground. Further, the structure support arrangement can be easily reused any number of times between different sites. Also, the recess for receiving the horizontal bar prevents the snaking of the structures.

Figure 10:
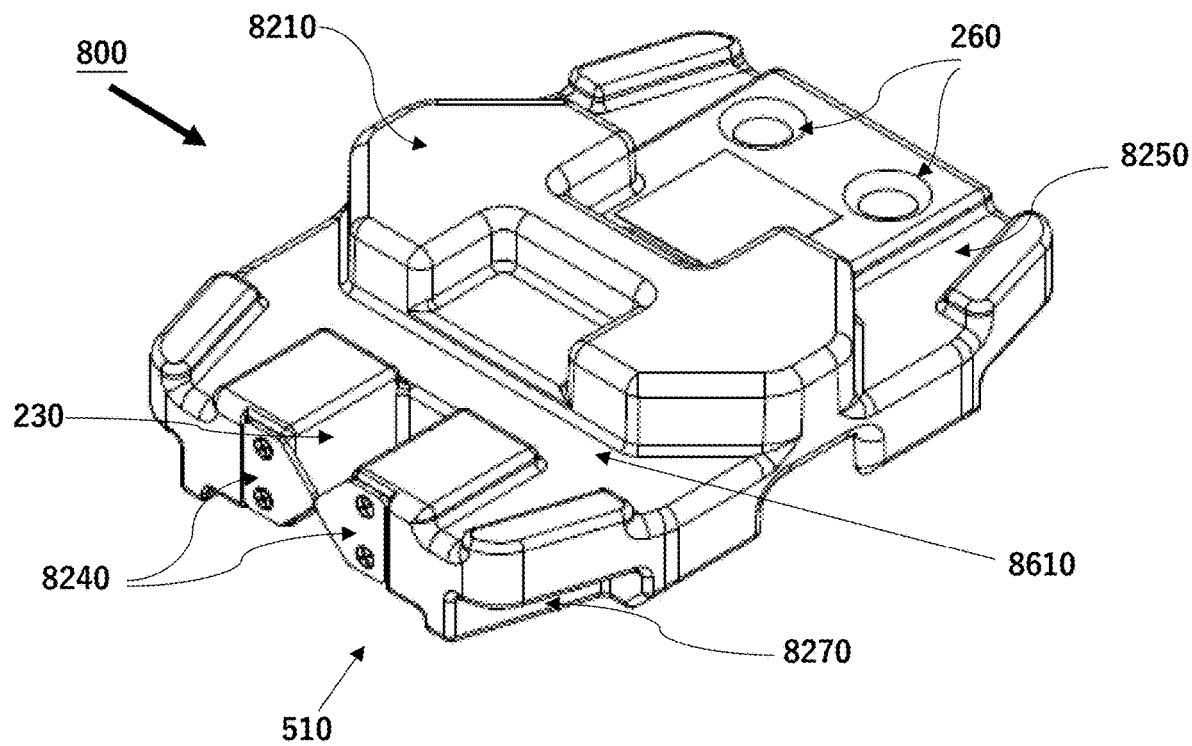
FIGS. 10 and 11 are front perspective views from a support side and a non-support side of a structure support arrangement in accordance with a further preferred embodiment of the present invention.
Figure 11:
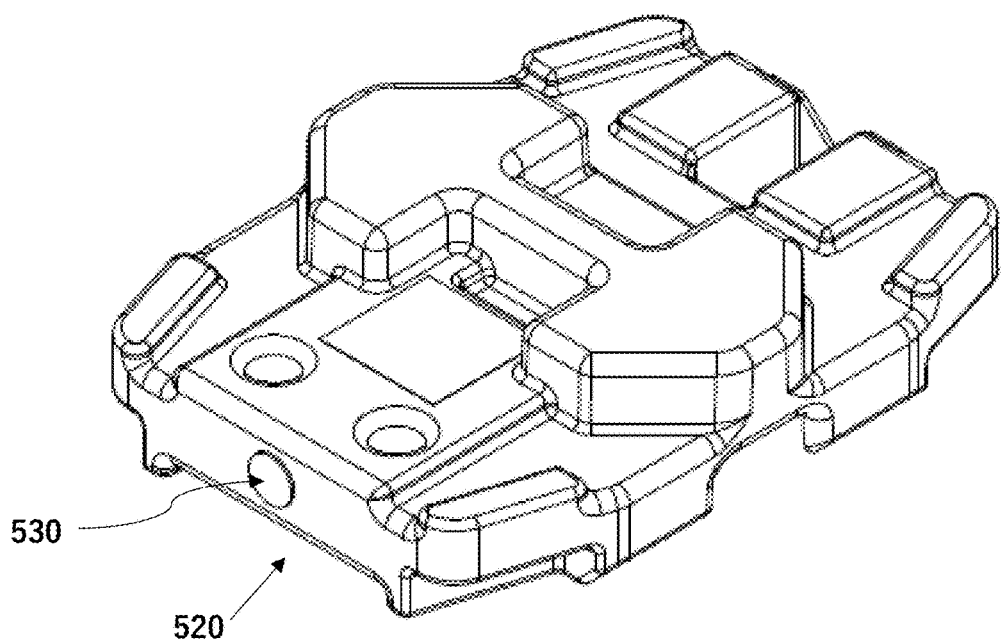
Figure 12:
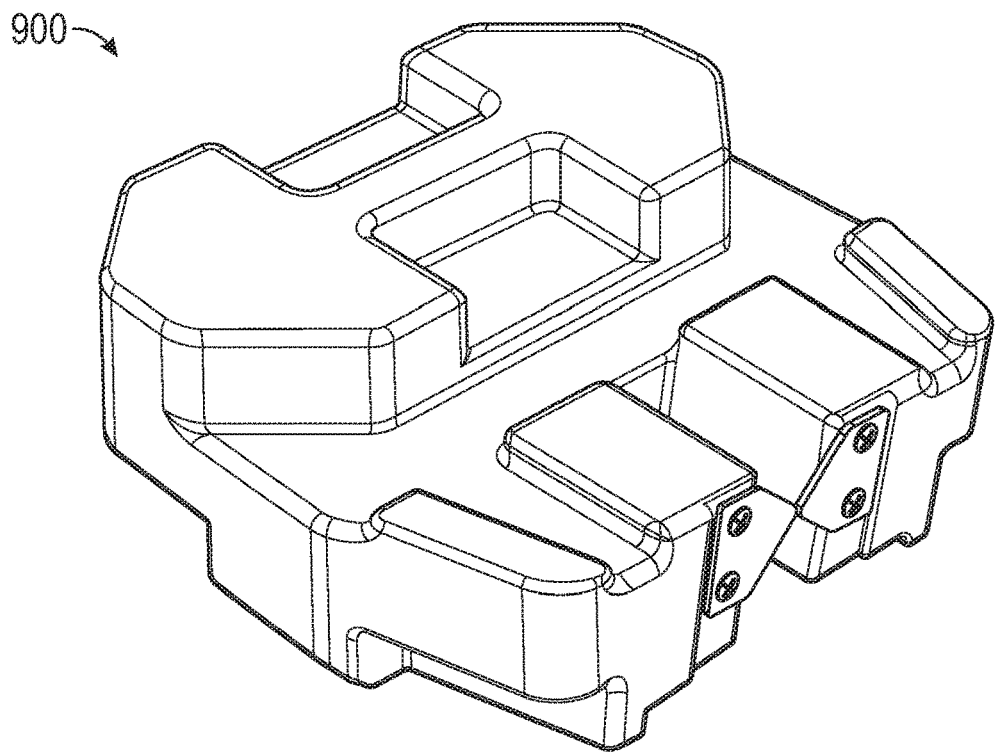
FIG. 12 illustrates a top perspective view of a half structure support arrangement in accordance with a preferred embodiment of the present invention, in which it omits the support post or fence post recesses.
Figure 13:
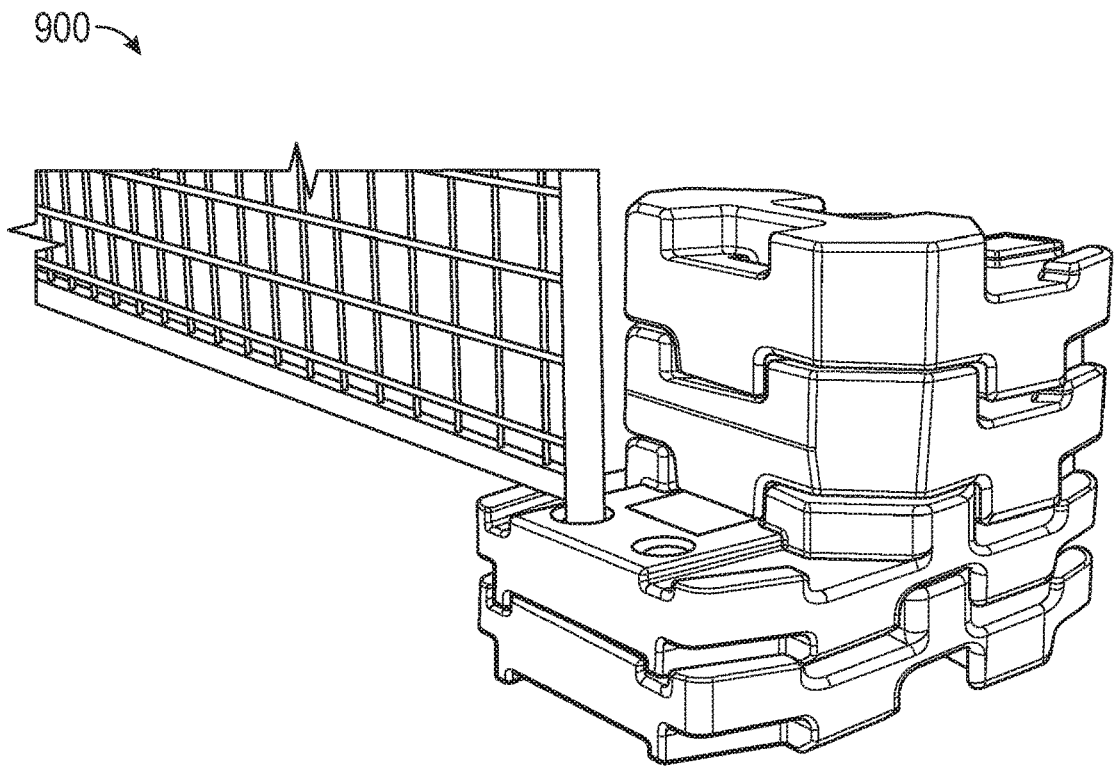
FIG. 13 illustrates a use of a plurality of half structure support arrangements of FIG. 12 with full structure support arrangements that have fence post recesses for mounting the fences at a low location while allowing further half support-weights to be added for greater counterweight.
Figure 14:
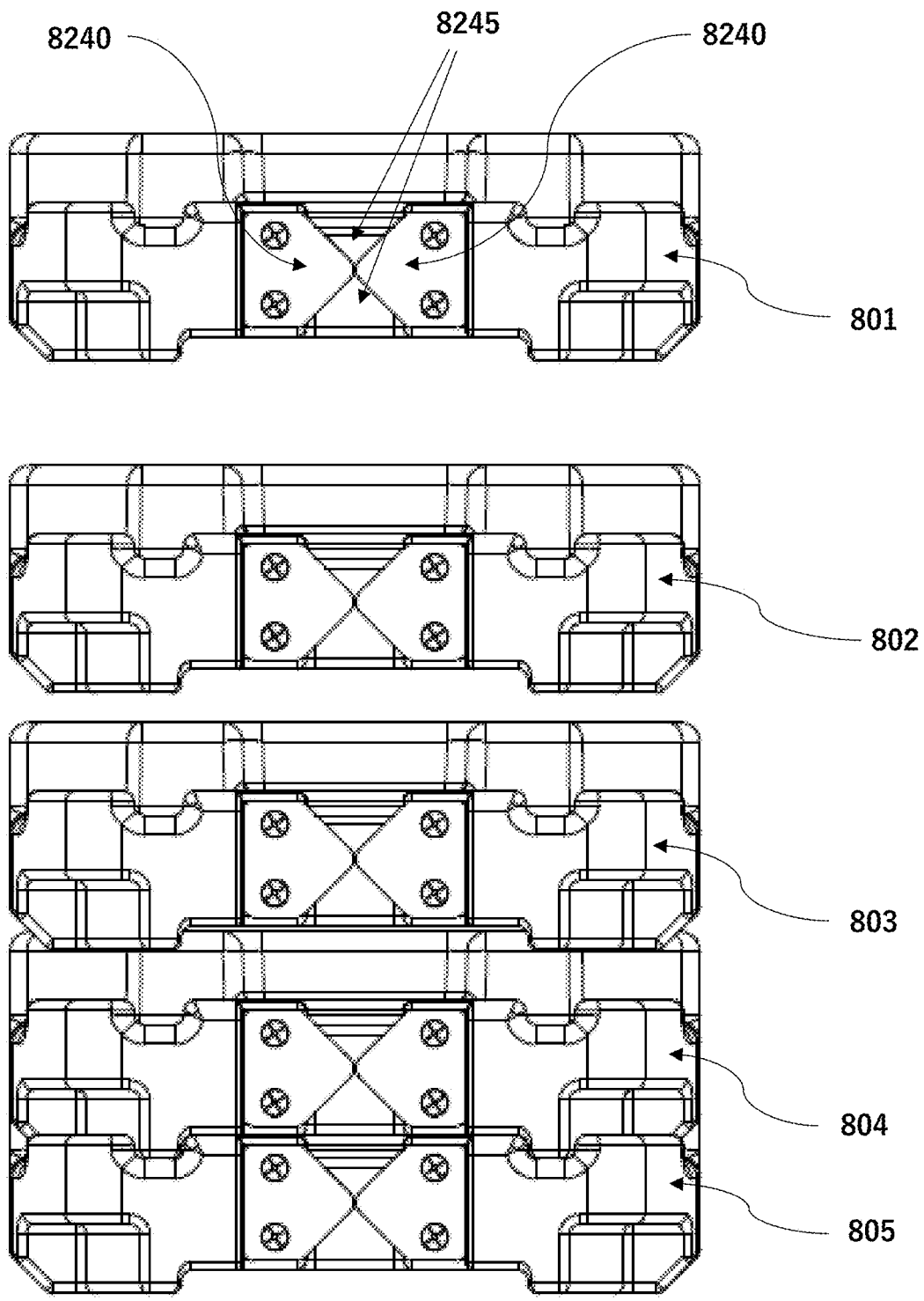
FIG. 14 is a front elevation of a plurality of structure support arrangements of FIG. 10 in process of forming a nestable stack.
Figure 15:
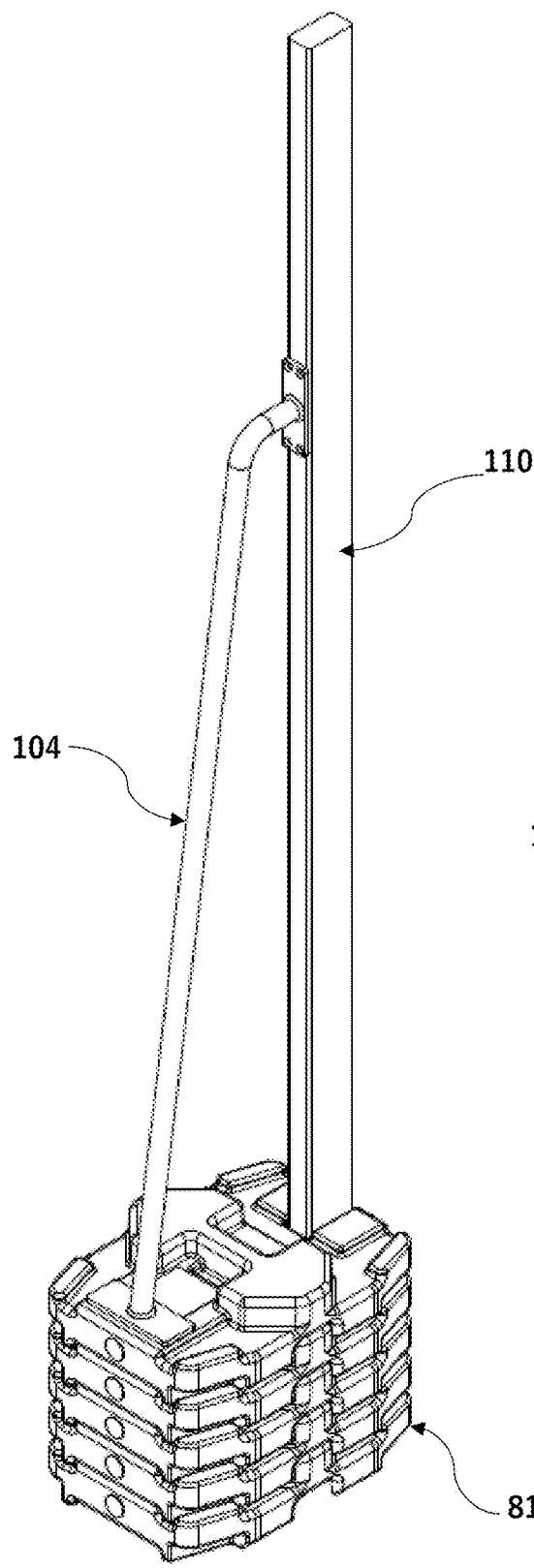
FIGS. 15 and 16 are front and rear views of a stack of structure support arrangements of FIG. 10 stacked along a support post and with a support post attached therebetween in accordance with a preferred embodiment of the present invention.

FIGS. 10 and 11 illustrates a structure support arrangement in accordance with yet another preferred embodiment 800 of the present invention. The body includes a dumbbell shaped projection 8210 which increases the number of planar circumferential plane walls to 16 compared with 12 planar circumferential plane walls of the I-shaped projection 2210 of earlier embodiments. This significantly increases the lateral location retention means when engaging with the complementary dumbbell shaped cavity on the underside of the adjacent structure support arrangement such as 801 in the stack of nestable structure support arrangements 801 to 805 of FIG. 14.

The counterweight 800 has two plates 8240 which are shaped with a rectangular outer portion for attaching by screws to the body of the counterweight and with triangular inner portions or lips that touch at their respective vertex. This substantially covers the lateral opening into the post receiving formation 230 that the support posts is inserted. The lateral opening is important to not allow escape of the support post out of the receiving recess. However, it has another benefit resulting from the size and shape of the lips 8240 which provide cut-away openings 8245 allowing direct access from the outer to the support post 110. This is particularly shown in the detail of FIG. 17 and wherein a board 120 can be directly connected to a post 110 when received in the post receiving formation 230 even along the portion within a stack 810 of nested structure support arrangements 800.

Figure 17:
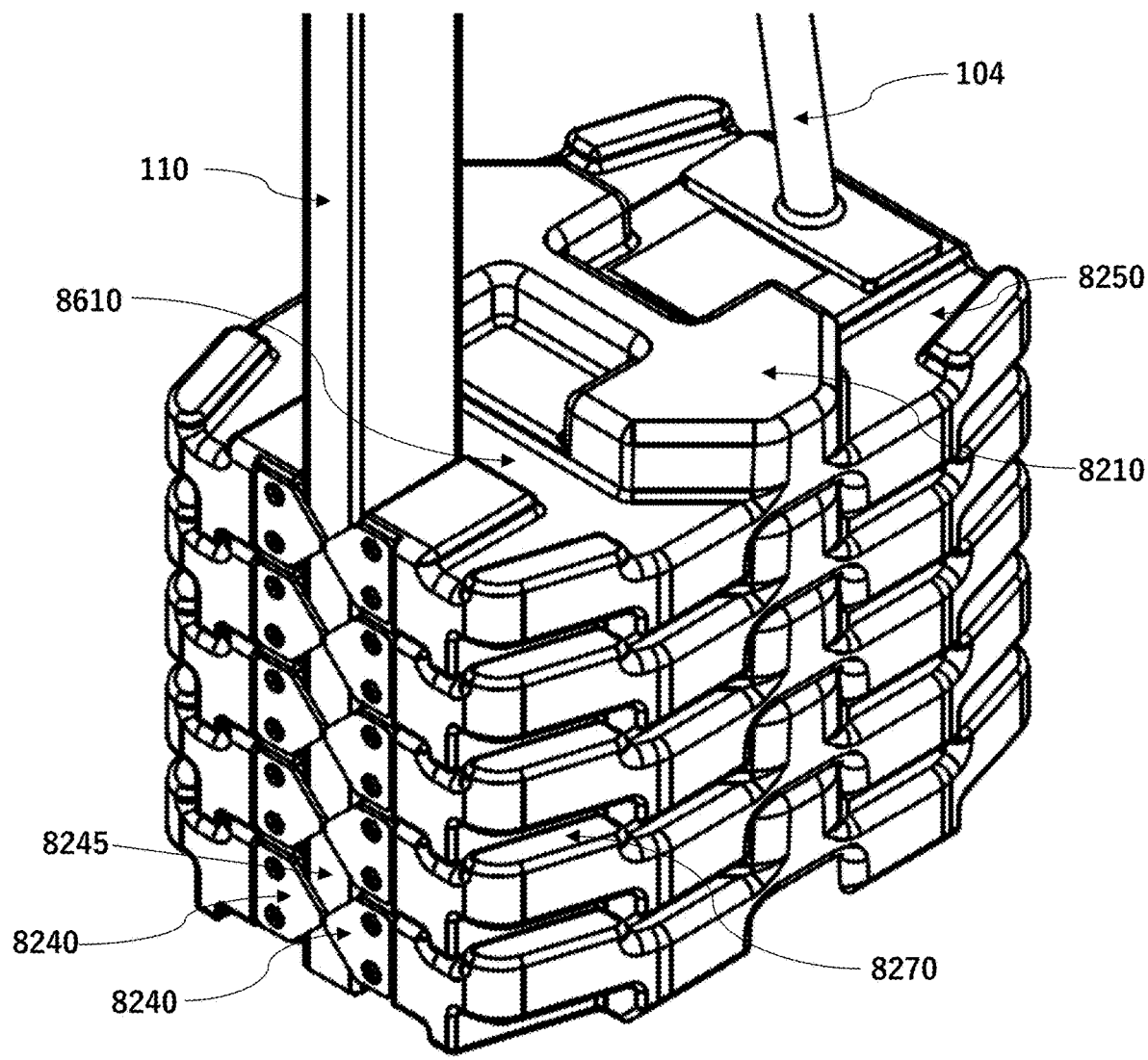
FIG. 17 is a detail of FIG. 16.

As shown in FIG. 10 and FIG. 17, the structure support arrangement 1220 further comprises a recess 8610 defined on the body member 210. The recess 8610 is provided along an entire width of the body member 210 with open ends at two sides of the structure support arrangement 1220, respectively. The recess 8610 is configured to receive a horizontal bar 730 that extends to a further structure support arrangement, particularly, into the corresponding recess 8610 of a top of a further structure support arrangement on an adjacent stack 810 to 813 of FIG. 18.

Further as shown in FIG. 17 the dovetail formations 250 of the earlier embodiments are modified to be open formations 8250 that still have projections that assist in preventing lateral motion of nested support-weights. However, when the structure support arrangement or support-weight is used in a fence support system such as in FIG. 17 the adjacent fence sections mounted in respective one of the fence post receiving recesses 260 can extend outwardly through the open sides of the open formations 8250 and allow the adjacent fence sections to be up to 90 degrees to each other. Therefore, the support weight can also form the function of a corner support of a fence system.

Figure 16:
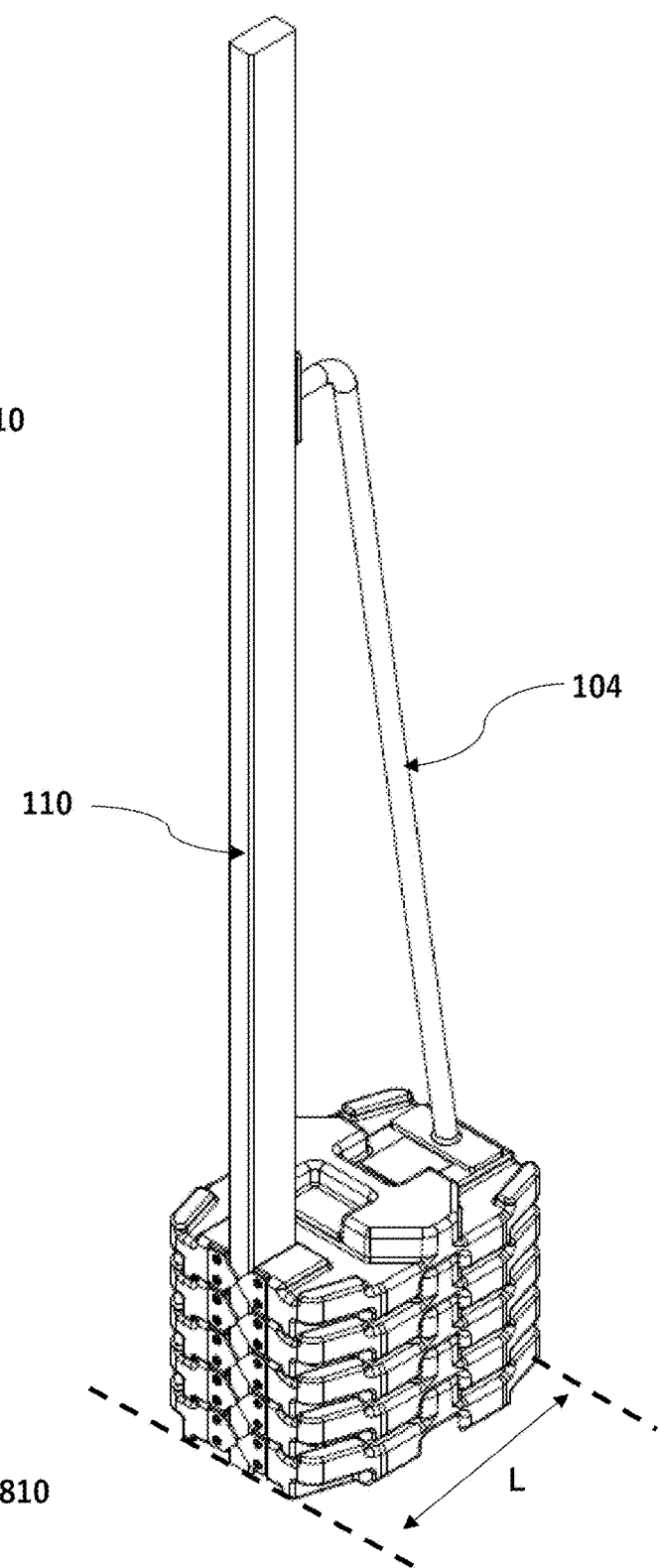
Figure 18:
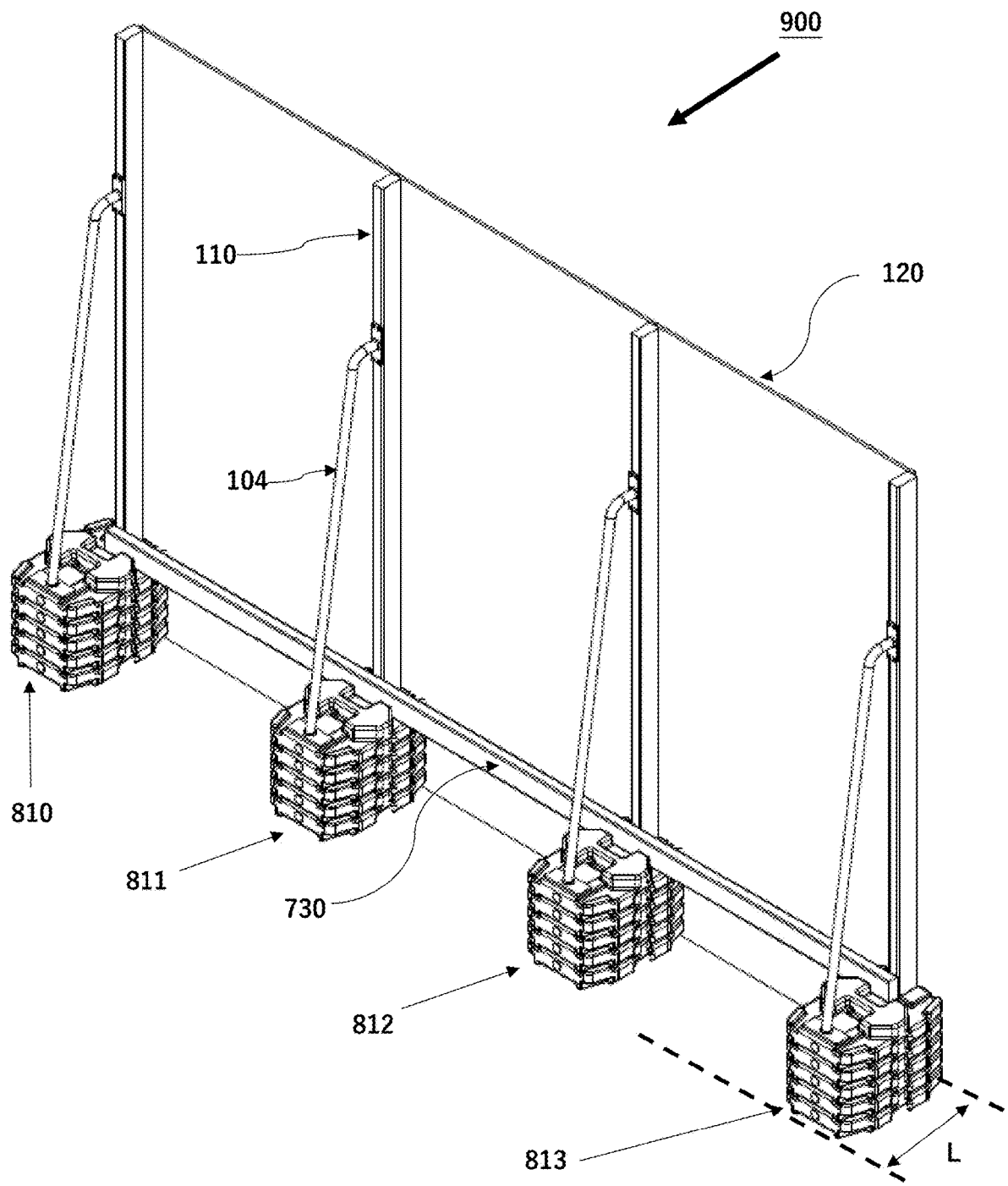
FIGS. 18 and 19 are perspective rear view and overhead view of an arrangement of plurality of stacks of structure support arrangements stacked along respective support posts and with respective support posts and cross member with attached boarding to form a hoarding in accordance with a preferred embodiment of the present invention.
Figure 19:
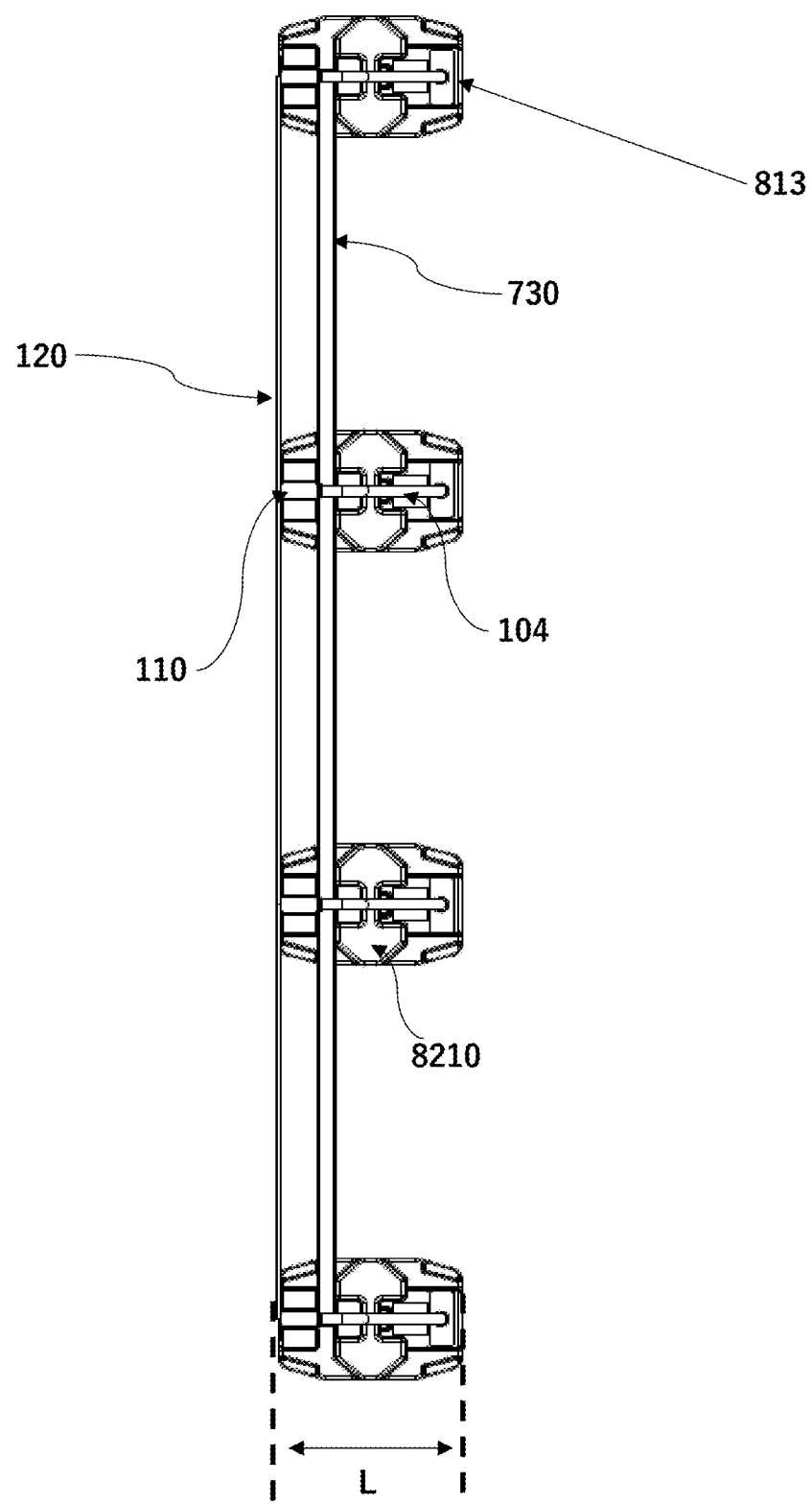

As shown in FIGS. 18 and 19, there is a hoarding installation including a hoarding panel 120, a panel support post 110, a plurality of stacks 810 to 813 of nestable support-weights 801 to 805, a strengthening post 104, and means to secure the hoarding panel to the panel support post. A further bracing horizontal bar fits within the lateral recess 8610 of the top support-weight of each similarly height stack and by the wedging in the recess between the support post 110 and the side of the open unused dumbbell shaped nesting projection 8210 of the top support weight provides lateral stability and integrity to the hoarding installation The post receiving formation 230 defined by the body of the support-weight 800 can directly receive a hoarding panel support post 110 to which a hoarding panel 120 is securable. This provides the advantage of avoiding any separate connector, extension, or other means to receive the panel support post which is outside the form of the weight and which may enlarge the footprint made by the combination of the weight and hoarding panel support post. Space for workers to operate behind a hoarding panel may be limited, so a small footprint is of great importance. Therefore, as seen by FIGS. 16, and 18 the footprint is limited to the length L of the support-weight A small footprint of the support-weight also results from: (i) the strengthening post being directly receivable by the support-weight; and/or (ii) the shape of the support-weight in a non-rectangular form with a wider central section (in plan view) permitting the mass of a stack of nestable support-weights to be located closer towards the hoarding panel so the weight extend less into the working space behind the hoarding than would be the case for comparable rectangular plan view shaped support-weight; and/or the nestability of the support-weights themselves.

The invention has fewer interoperating parts than other systems in the prior art. For a hoarding installation the invention requires only three components separate from the hoarding panel, and for a fencing installation the invention requires only one component separate from the fencing panel.

The invention provides for easy stacking of the support-weights using handle formations 8270 so that a support-weight can be picked up and put down without trapping the operator's fingers. Angled corners also allow the weights to be safely stacked on pallets, where abutting stacks of weights would again inhibit the operator's ability to safely handle the weights. The weights are also adapted to be a convenient size and weight for lifting. Other advantages due to the size and shape of the weights are gained in that fewer weights (compared with prior art systems) are required to be used in conjunction with the strengthening post to achieve certification of relevant industry standards. See, for example, Australian Standards AS4687-2007—"Temporary Fencing and Hoardings" and AS1170.2-2011—"Structural design actions—Wind actions".

Use of the strengthening support post 104 raises the fulcrum point of a hoarding installation so that it is higher than it would be without the use of the support post. This means that collapsing of the hoarding installation is inhibited when subject to forces against a hoarding panel.

The orientation of a panel support post 110 having a rectangular cross-section such that the wider dimension of the panel support post is perpendicular to the near edge of the support-weight and thereby rectilinear to the hoarding panel 120. This orientation is different to the prior art in which has the wider dimension of the panel support post run parallel with the near edge of the support-weight. This perpendicular direction, providing longitudinal alignment of the long axis of the cross sectional shape of the panel support post 110 with the longitudinal length of the support-weight 800, which is also coaxial with the direction of extension of the support post of the first connection means from the support post, provides substantial strength gains, as the forces on the panel support post are concentrated about the deep axis of the post (for example, in a commonly available shaped post, approximately 90 mm deep) instead of the shallow axis of the stud (for example, in a commonly available shaped post, approximately 45 mm deep).

The invention is able to used with panel support posts 110 of a standard size (for example, a "2×4" which is approximately 40 mm×90 mm) and meet the relevant industry standards. The invention is able to be used with standard grade panel support posts (for example, a MPG10 grade timber stud).

Where a system is not braced (for example, by attachment to a wall or ceiling) lateral, post installation movement or "snaking" could occur. To avoid this, the invention contemplates use of a horizontal bar 730 received into a complementary recess 8610 in the uppermost support-weight 800 of a hoarding installation. The horizontal bar may also be affixed to one or more panel support posts 110 (for example, by means of affixing means (such as a screw) between the panel support post and the horizontal bar and/or the hoarding panel.

The invention provides the user the ability to install a pre-certified and structural engineer approved counterweight solution. The user is able to follow a simple process and ensure that the panels are secure, and the system is safe.

Once a hoarding installation is complete, the support-weights 800 cannot be removed without first removing the panels 120 (which are the area of risk if impacted). By comparison in the prior art which uses an upright stand, the weights can be added and removed without removing the panel and this is not tamperproof, but since the panels of a hoarding installation in accordance with invention may screwed into the panel support post (in the space between the plates), once the panel is secured to the panel support posts, the support-weights cannot be removed until after the screws affixing the hoarding are removed, and (by extension) the hoarding panel itself.

Embodiments

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment but may. Furthermore, the particular features, structures or characteristics may be combined in any suitable manner, as would be apparent to one of ordinary skill in the art from this disclosure, in one or more embodiments.

Similarly, it should be appreciated that in the above description of example embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the Detailed Description of Specific Embodiments are hereby expressly incorporated into this Detailed Description of Specific Embodiments, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

It should be noted that the aspects of the methods and systems including its preferred embodiments as outlined in the present patent application may be used stand-alone or in combination with the other aspects of the methods and systems disclosed in this document. Furthermore, all aspects of the methods and systems outlined in the present patent application may be arbitrarily combined. In particular, the features of the claims may be combined with one another in an arbitrary manner.

Different Instances of Objects

As used herein, unless otherwise specified the use of the ordinal adjectives "first", "second", "third", etc., to describe a common object, merely indicate that different instances of like objects are being referred to and are not intended to imply that the objects so described must be in a given sequence, either temporally, spatially, in ranking, or in any other manner.

Specific Details

In the description provided herein, numerous specific details are set forth. However, it is understood that embodiments of the invention may be practiced without these specific details. In other instances, well-known methods, structures and techniques have not been shown in detail in order not to obscure an understanding of this description.

Terminology

In describing the preferred embodiment of the invention illustrated in the drawings, specific terminology will be resorted to for the sake of clarity. However, the invention is not intended to be limited to the specific terms so selected, and it is to be understood that each specific term includes all technical equivalents which operate in a similar manner to accomplish a similar technical purpose. Terms such as "forward", "rearward", "radially", "peripherally", "upwardly", "downwardly", "top", "bottom", "under" and the like are used as words of convenience to provide reference points and are not to be construed as limiting terms.

For the purposes of this specification, the term "plastic" shall be construed to mean a general term for a wide range of synthetic or semisynthetic polymerization products, and generally including a hydrocarbon-based polymer.

As used herein the term "and/or" means "and" or "or", or both.

As used herein "(s)" following a noun means the plural and/or singular forms of the noun.

Comprising and Including

In the claims which follow and in the preceding description of the invention, except where the context requires otherwise due to express language or necessary implication, the word "comprise" or variations such as "comprises" or "comprising" are used in an inclusive sense, i.e. to specify the presence of the stated features but not to preclude the presence or addition of further features in various embodiments of the invention.

Any one of the terms: including or which includes or that includes as used herein is also an open term that also means including at least the elements/features that follow the term, but not excluding others. Thus, including is synonymous with and means comprising.

Scope of Invention

Thus, while there has been described what are believed to be the preferred embodiments of the invention, those skilled in the art will recognize that other and further modifications may be made thereto without departing from the spirit of the invention, and it is intended to claim all such changes and modifications as fall within the scope of the invention. Functionality may be added or deleted from the block diagrams and operations may be interchanged among functional blocks. Steps may be added or deleted to methods described within the scope of the present invention.

Although the invention has been described with reference to specific examples, it will be appreciated by those skilled in the art that the invention may be embodied in many other forms.

INDUSTRIAL APPLICABILITY

It is apparent from the above, that the arrangements described are applicable to construction, advertising, maintenance services industries, and other applicable industries.

Although a preferred embodiment of this invention has been disclosed, a worker of ordinary skill in this art would recognize that certain modifications would come within the scope of this invention. For that reason, the following claims should be studied to determine the true scope and content of this invention.

What is claimed is:

1. A structure support arrangement for supporting a structure, the structure support arrangement comprising:
   a. a counterweight including:
      i. a body member;
      ii. a nesting formation defined on the body member; and
      iii. a post receiving formation defined on the body member and configured for directly receiving a support post that is securable to, or part of, the structure to support the structure;
   b. a strength enhancing structure for enhancing strength of the structure support arrangement, the strength enhancing structure comprising:
      i. a main body;
      ii. a first connection mechanism at a first end of the main body for connection to the counterweight, wherein the first connection mechanism includes a first connection plate for connection with an upper side of the counterweight, and the first connection plate is parallel to the upper side of the counterweight; and
      iii a second connection mechanism at a second end of the main body for connection to the support post, wherein the second connection mechanism includes a second connection plate extending from the second end of the main body, and the second connection plate is transverse to the upper side of the counterweight,
   wherein the strength enhancing structure is configured such that the first connection mechanism is connectable towards a first end of the counterweight, and the post receiving formation is located towards a second end of the counterweight that opposes the first end of the counterweight, and at least a portion of the main body of the strength enhancing structure, when connected to the counterweight, extends upwardly from the first end of the counterweight and diagonally towards the support post at an angle relative to the support post.

2. The structure support arrangement according to claim 1, wherein the strength enhancing structure is connectable to an upper counterweight of a plurality of nested counterweights.

3. The structure support arrangement according to claim 1, wherein the counterweight includes one or more apertures or recesses defined on the body member for receiving the first connection mechanism of the strength enhancing structure.

4. The structure support arrangement according to claim 3, wherein the one or more apertures or recesses are located towards an end of the counterweight.

5. The structure support arrangement according to claim 4, wherein each said one or more apertures or recesses are configured to receive a fence post of a fence panel.

6. The structure support arrangement according to claim 1, wherein the first connection mechanism includes at least one connection bar.

7. The structure support arrangement according to claim 6, further comprising a plurality of nested counterweights wherein the at least one connection bar is receivable into an uppermost two of said counterweights of said plurality of nested counterweights.

8. The structure support arrangement according to claim 6, wherein the first connection plate extends from the first end of the main body, and the at least one connection bar extends from the first connection plate.

9. The structure support arrangement according to claim 1, wherein the second connection mechanism includes at least one hole extending through the second connection plate.

10. The structure support arrangement according to claim 9, wherein the strength enhancing structure includes at least one fastener to securely connect the second connection mechanism to the support post through the at least one hole.

11. The structure support arrangement according to claim 1, wherein the counterweight of the structure support arrangement further comprises a recess defined on the body member and configured to receive a horizontal bar that is adapted to extend to be received in a corresponding recess of another counterweight in an adjacent structure support arrangement, and to thereby inhibit displacement of the counterweight and the adjacent structure support arrangement.

12. The structure support arrangement according to claim 1, wherein the strength enhancing structure is adapted to create a triangular relationship between the counterweight, or a stack of the counterweights, and the support post, such that the counterweight, an uppermost counterweight in the stack of counterweights, forms a horizontal base of a triangle, the support post extends perpendicular to the counterweight and forms a vertical height of the triangle, and the strength enhancing structure forms a hypotenuse between the horizontal base and the vertical height of the triangle, to increase the stability of the structure support arrangement.

13. The structure support arrangement according to claim 1, wherein the counterweight includes at least one exterior support side along which the structure is configured to be abutted against and supported in operation.

14. The structure support arrangement according to claim 13, wherein the post receiving formation is located adjacent to the at least one exterior support side and includes an opening formed on the at least one exterior support side.

15. The structure support arrangement according to claim 14, wherein the counterweight further comprises one or more plates securable to the body member, in proximity of the post receiving formation, the one or more plates extending over the opening to at least partially cover the opening.

16. The structure support arrangement according to claim 15, wherein when the support post is received in the post receiving formation a hoarding panel is securable to the support post by securing means extending through the opening defined by the one or more plates.

17. The structure support arrangement according to claim 16, wherein when the counterweight is nested with a further counterweight, a gap is formed between the one or more plates of the counterweight and said further counterweight such that the securing means can be inserted through the hoarding panel and the gap and into the support post to secure the counterweight to the panel and the support post.

18. A method of installing a hoarding structure support arrangement including a hoarding panel, a hoarding panel support post that is securable to the hoarding panel, and a structure support arrangement comprising:
   a. a counterweight including:
      i. a body member,
      ii. a nesting formation defined on the body member; and
      iii. a post receiving formation defined on the body member and configured for directly receiving the hoarding panel support post to support the structure:
   b. a strength enhancing structure for enhancing strength of the hoarding structure support arrangement, the strength enhancing structure comprising:
      i. a main body;
      ii. a first connection mechanism at a first end of the main body for connection to the counterweight, wherein the first connection mechanism includes a first connection plate for connection with an upper side of the counterweight, and the first connection plate is parallel to the upper side of the counterweight; and
      iii a second connection mechanism at a second end of the main body for connection to the hoarding panel support post, wherein the second connection mechanism includes a second connection plate extending from the second end of the main body, and the second connection plate is transverse to the upper side of the counterweight;
   wherein the strength enhancing structure is configured such that the first connection mechanism is connectable towards a first end of the counterweight, and the post receiving formation is located towards a second end of the counterweight that opposes the first end of the counterweight, and at least a portion of the main body of the strength enhancing structure, when connected to the counterweight, extends upwardly from the first end of the counterweight and diagonally towards the support post at an angle relative to the support post;

the method including the steps of:
   stacking a plurality of the counterweights one on top of the other;
   inserting the hoarding panel support post into the post receiving formation;
   connecting the strength enhancing structure to at least one of the plurality of counterweights;
   fastening the strength enhancing structure to the hoarding panel support post; and
   securing the hoarding panel to the hoarding panel support post.

* * * * *